United States Patent
Bae et al.

(10) Patent No.: US 8,822,463 B2
(45) Date of Patent: Sep. 2, 2014

(54) METHYLCYCLOHEXANE DERIVATIVES AND USES THEREOF

(75) Inventors: Sung Jin Bae, Daejeon (KR); Han Ju Yi, Daejeon (KR); Sun Gwan Hwang, Daejeon (KR); Mo Ses Jeong, Daejeon (KR); Yeo Jin Yoon, Daejeon (KR); Sang Mi Chae, Daejeon (KR); Joo Young Park, Daejeon (KR); Eun Ju Ryu, Daejeon (KR)

(73) Assignee: Sk Biopharmaceuticals Co., Ltd., Seoul (KR)

( * ) Notice: Subject to any disclaimer, the term of this patent is extended or adjusted under 35 U.S.C. 154(b) by 0 days.

(21) Appl. No.: 13/876,803

(22) PCT Filed: Sep. 28, 2011

(86) PCT No.: PCT/KR2011/007117
§ 371 (c)(1),
(2), (4) Date: Apr. 30, 2013

(87) PCT Pub. No.: WO2012/044046
PCT Pub. Date: Apr. 5, 2012

(65) Prior Publication Data
US 2013/0217686 A1 Aug. 22, 2013

(30) Foreign Application Priority Data
Sep. 29, 2010 (KR) .................. 10-2010-0094463

(51) Int. Cl.
| | | |
|---|---|---|
| C07D 401/12 | (2006.01) | |
| C07D 207/06 | (2006.01) | |
| C07D 213/55 | (2006.01) | |
| C07D 295/14 | (2006.01) | |
| C07D 213/40 | (2006.01) | |
| C07D 213/75 | (2006.01) | |
| C07D 213/79 | (2006.01) | |
| C07D 295/205 | (2006.01) | |
| C07D 213/61 | (2006.01) | |
| C07D 213/53 | (2006.01) | |
| C07D 213/80 | (2006.01) | |
| C07D 213/30 | (2006.01) | |
| C07D 213/89 | (2006.01) | |

(52) U.S. Cl.
CPC .......... *C07D 401/12* (2013.01); *C07D 213/40* (2013.01); *C07D 213/75* (2013.01); *C07D 207/06* (2013.01); *C07D 295/14* (2013.01); *C07D 213/55* (2013.01); *C07D 213/79* (2013.01); *C07D 295/205* (2013.01); *C07D 213/61* (2013.01); *C07D 213/53* (2013.01); *C07D 213/80* (2013.01); *C07D 213/30* (2013.01); *C07D 213/89* (2013.01)
USPC .............. 514/235.5; 514/253.01; 514/255.01; 514/318; 514/343; 514/423; 544/131; 544/360; 544/389; 546/194; 546/279.1; 548/531

(58) Field of Classification Search
None
See application file for complete search history.

(56) References Cited

U.S. PATENT DOCUMENTS

| 2007/0082956 A1 | 4/2007 | Magerl et al. |
| 2009/0181920 A1 | 7/2009 | Watkins et al. |

FOREIGN PATENT DOCUMENTS

| JP | 06087810 | 3/1994 |
| WO | 2009077527 | 6/2009 |
| WO | 2009/146539 | 12/2009 |

OTHER PUBLICATIONS

Extended European Search Report for Application No. 11829552.6 dated Feb. 24, 2014 (5 pages).
PCT/KR2011/007117 International Search Report and Written Opinion dated Apr. 18, 2012, 4 pages.
Aley et al., "Nitric Oxide Signaling in Pain and Nociceptor Sensitization in the Rat" The Journal of Neuroscience, Sep. 1, 1998, 18(17):7008-7014.
Bonnefous et al., "Discovery of Inducible Nitric Oxide Synthase (iNOS) Inhibitor Development Candidate KD7332, Part 1: Identification of a Novel, Potent, and Selective Series of Quinolinone iNOS Dimerization Inhibitors that are Orally Active in Rodent Pain Models" J. Med. Chem. 2009, 52, 3047-3062.
Chen et al., "Nitric oxide synthase modulates CFA-induced thermal hyperalgesia through cytokine regulation in mice" Molecular Pain 2010, 6:13, 1-11.
Florio et al., "Disruption of nNOS-PSD95 protein-protein interaction inhibits acute thermal hyperalgesia and chronic mechanical allodynia in rodents" British Journal of Pharmacology (2009), 158, 494-506.
Freire et al., "Pain modulation by nitric oxide in the spinal cord" Frontiers in Neuroscience, vol. 3(2), Sep. 15, 2009, 175-181.
Harris et al., "Disease Biomarkers in Multiple Sclerosis, Potential for Use in Therapeutic Decision Making" Mol Diagn Ther 2009, 13(4) 225-244.
Tanabe et al., "Pharmacological assessments of nitric oxide synthase isoforms and downstream diversity of NO signaling in the maintenance of thermal and mechanical hypersensitivity after peripheral nerve injury in mice" Neuropharmacology 56 (2009) 702-708.

*Primary Examiner* — Janet L Andres
*Assistant Examiner* — Timothy R Rozof
(74) *Attorney, Agent, or Firm* — Michael Best & Friedrich LLP

(57) ABSTRACT

A novel methylcyclohexane derivative, and a pharmaceutical composition including the same that is effective for the prevention or treatment of pain.

8 Claims, 1 Drawing Sheet

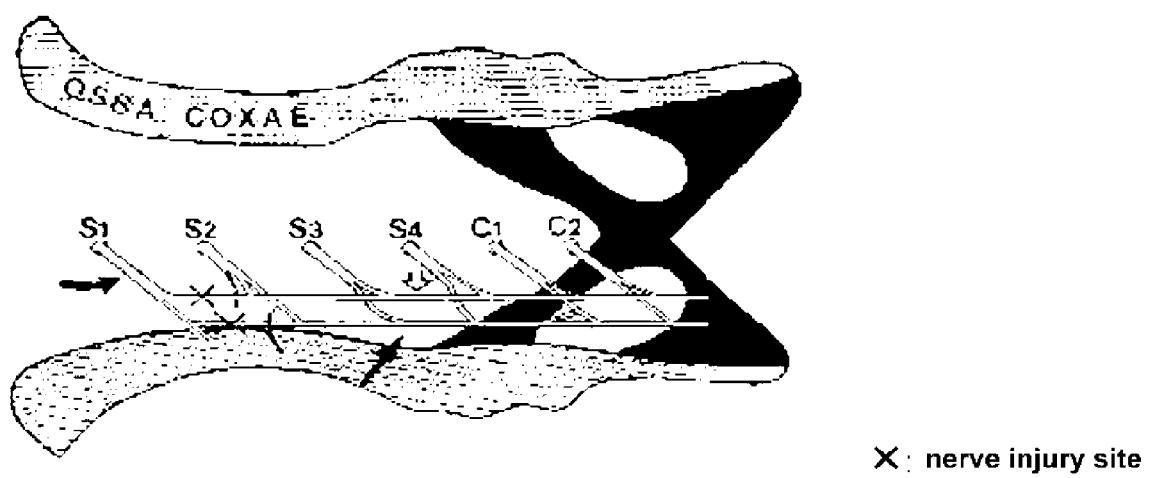
X : nerve injury site

METHYLCYCLOHEXANE DERIVATIVES AND USES THEREOF

CROSS-REFERENCE TO RELATED APPLICATIONS

This application is a national stage filing under 35 U.S.C. §371 of International Application No. PCT/KR2011/007117, filed on Sep. 28, 2011, which claims the benefit of Korean Patent Application No. 10-2010-0094463, filed on Sep. 29, 2010, in the Korean Intellectual Property Office, the disclosure of which is incorporated herein in its entirety by reference.

TECHNICAL FIELD

Background Art

Nitric oxide (NO) is a signal transduction molecule that is present in a gaseous phase in vivo and functions as a critical messenger in terms of physiology and pathology. If the NO concentration is appropriate, NO protects organs from ischemic diseases. However, if the NO concentration is too high, NO acts as a toxic material in living tissues and causes a vascular collapse such as a septic shock.

It is reported that NO functions as a major element that causes pain (hyperalgesia), and an NO synthase inhibitor reduces enhanced hyperalgesia (*J. Neurosci.*, 18(17):7008-7014, 1998; *Mol. Pain*, 6:13, 2010). In particular, it is also reported that NO functions as a major element that causes various types of pain including inflammatory pain, nociceptive pain, and neuropathic pain, and if the NO signal transfer or the production of NO is suppressed in various animal models, pain is suppressed (*J. Neurosci.*, 18(17):7008-7014, 1998; *Mol. Pain*, 6:13, 2010; *Mol. Diagn. Ther.*, 13(4):225-244, 2009; *Front Neurosci.* 3(2):175-181, 2009; *Br. J. Pharmacol.*, 158(2):494-506, 2009; *J. Med. Chem.*, 52(9):3047-3062, 2009; *Neuropharmacology*, 56(3):702-708, 2009).

Based on these results, various NO production inhibitors for various indications are commercially available, or are being developed in a clinical phase.

DISCLOSURE OF INVENTION

Technical Problem

The present invention provides a compound selected from the group consisting of a novel methylcyclohexane derivative, and a pharmaceutically acceptable salt, isomer, solvate, and hydrate of the novel methylcyclohexane derivative, and a combination thereof.

The present invention also provides a pharmaceutical composition for the prevention or treatment of pain, wherein the pharmaceutical composition includes a therapeutically effective amount of a novel methylcyclohexane derivative; and a pharmaceutically acceptable carrier.

The present invention also provides a method of treating pain using the pharmaceutical composition.

Solution to Problem

According to an aspect of the present invention, there is provided a compound selected from the group consisting of a methylcyclohexane derivative represented by Formula I below and a pharmaceutically acceptable salt, isomer, solvate, and hydrate of the methylcyclohexane derivative, and a combination thereof.

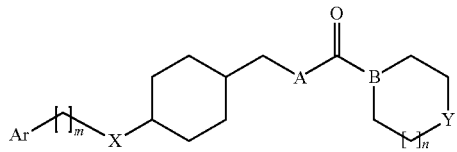

Formula I wherein
Ar is selected from the group consisting of phenyl, pyridine, and pyridine-N-oxide, each of which is substituted with one or more identical or different substituents selected from the group consisting of a hydrogen atom, a linear or branched C1 to C6 alkyl, halogen, a linear or branched C1 to C6 alkoxy, and trifluoromethyl;
X is O, (C=O)O, $NR_1$(C=O)O, NH, (C=O)NH, or O(C=O)NH; and $R_1$ is H or $CH_3$;
Y is $CH_2$, O, or N—$R_2$; $R_2$ is H or $CH_3$;
A is O or NH;
B is CH or N; and
m is an integer between 0 and 2 and n is 0 or 1.

Compounds represented by Formula I may be easily manufactured from known compounds or compounds that are easily prepared therefrom, with reference to Reaction Schemes I through VII, by one of those ordinary skill in the art that has common knowledge in synthesizing compounds. Accordingly, the following method of manufacturing the compound represented by Formula I above is only an example, and if desired, a process sequence may be selectively altered and the present invention is not limited thereto.

Reaction Scheme I

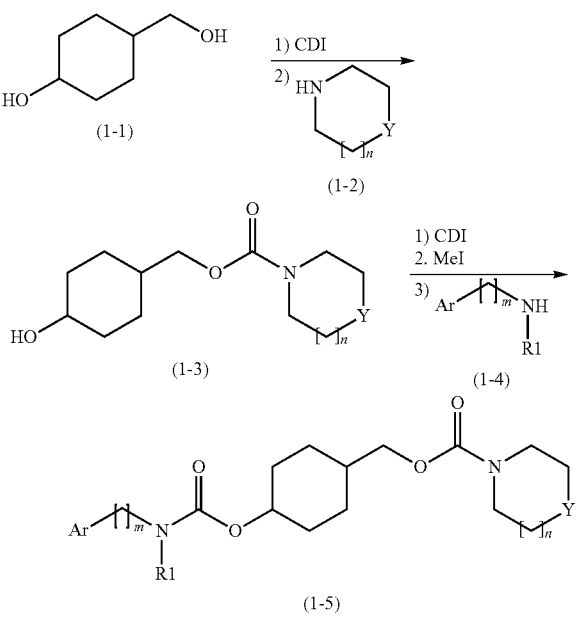

As illustrated in Reaction Scheme I above, Compound (1-1) is reacted with 1,1-carbonyldiimidazole (CDI), and then reacted with various amines (for example, Compound (1-2)) to synthesize Compound (1-3). Thereafter, Compound (1-3) is reacted with CDI and methyl iodide and then reacted with various amines (for example, Compound (1-4)) to obtain Compound (1-5).

Reaction Scheme II

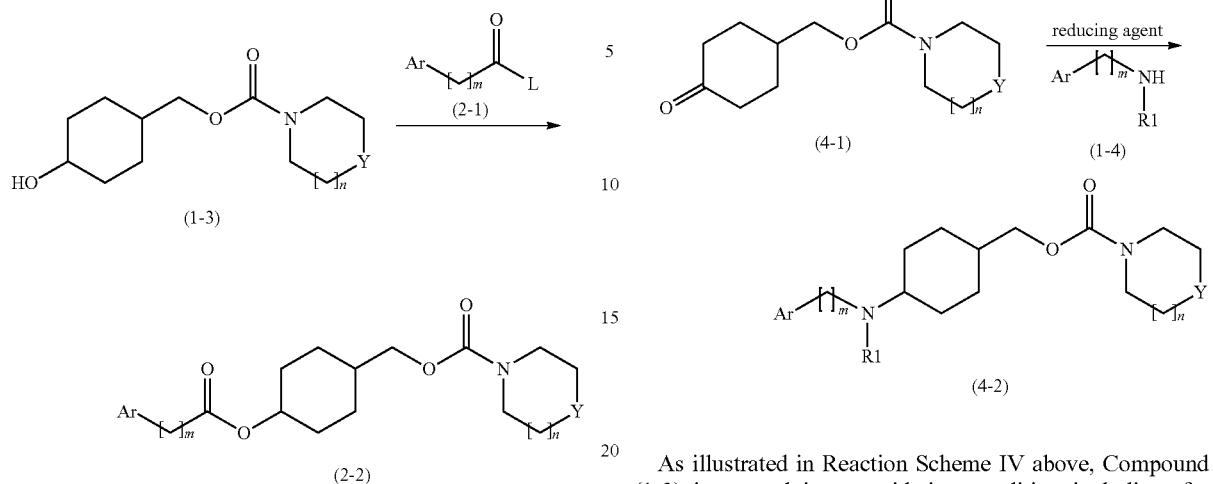

As illustrated in Reaction Scheme II above, Compound (1-3) is reacted with various carbonyl compounds (for example, Compound (2-1)) including a leaving group such as Cl to obtain Compound (2-2). In Reaction Scheme II, L represents the leaving group

Reaction Scheme III

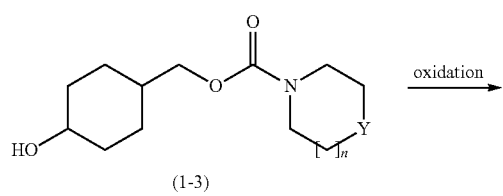

As illustrated in Reaction Scheme III above, Compound (1-3) is reacted with a base, such as NaH, and then reacted with various compounds (for example, Compound (3-1)) including a leaving group such as Br to obtain Compound (3-2).

Reaction Scheme IV

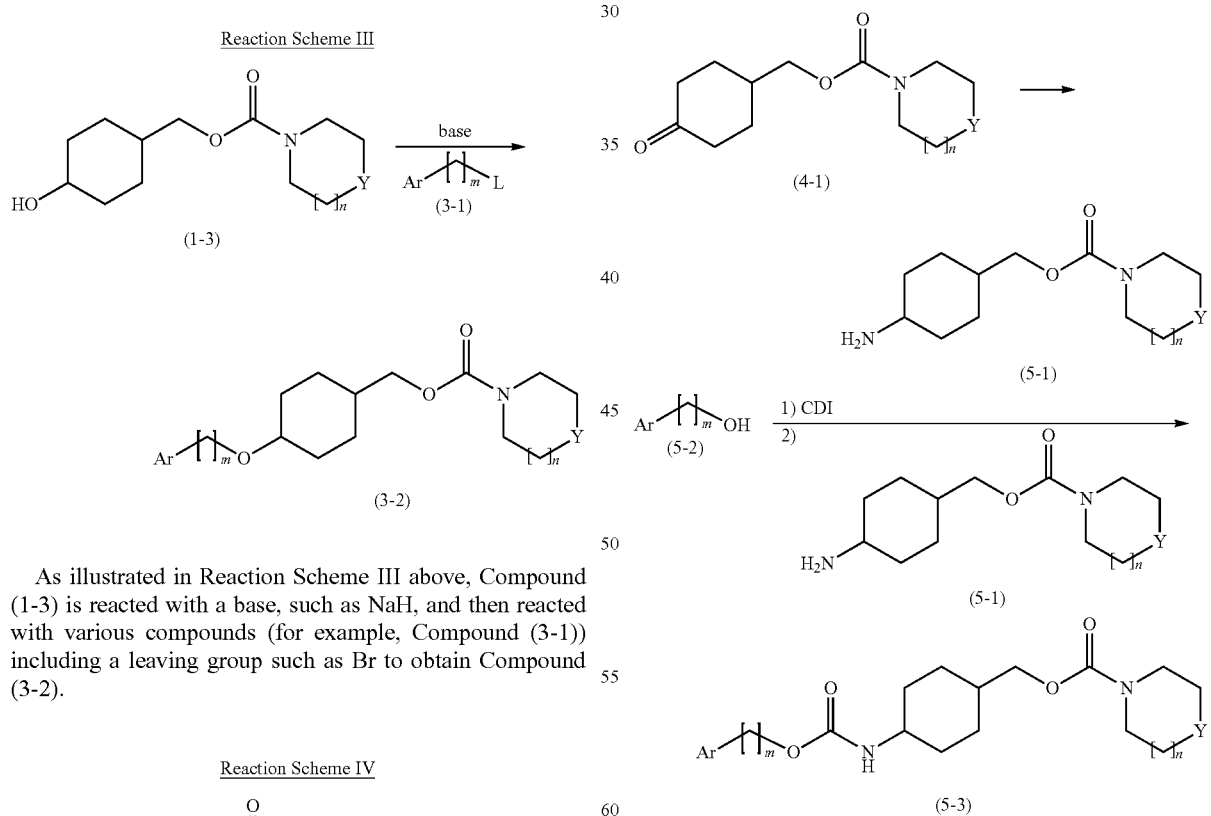

As illustrated in Reaction Scheme IV above, Compound (1-3) is reacted in an oxidation condition including, for example, TEMPO or oxone to synthesize oxidized Intermediate (4-1). Intermediate (4-1) is reacted with various amines (for example, Compound (1-4)) in the presence of a reducing agent, such as NaBH(OAc)$_3$, to obtain Compound (4-2).

Reaction Scheme V

As illustrated in Reaction Scheme V above, Compound (4-1) is formed as an oxime and then Intermediate (5-1) is synthesized through hydrogenation. Various alcohols (for example, Compound (5-2)) is reacted with CDI and then reacted with Intermediate (5-1) to obtain Compound (5-3).

Reaction Scheme VI

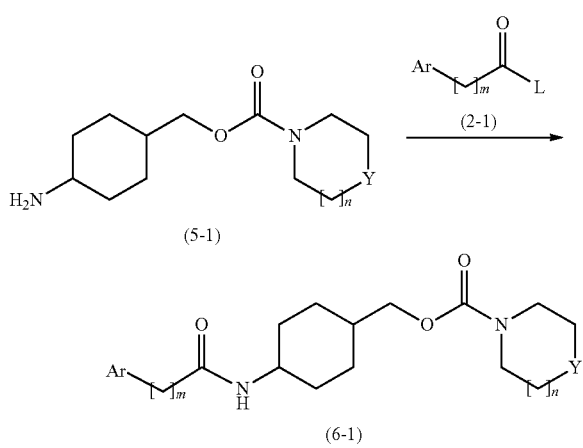

As illustrated in Reaction Scheme VI above, Compound (5-1) is reacted with various carbonyl compounds (for example, Compound (2-1)) including a leaving group such as Cl to obtain Compound (6-1).

Reaction Scheme VII

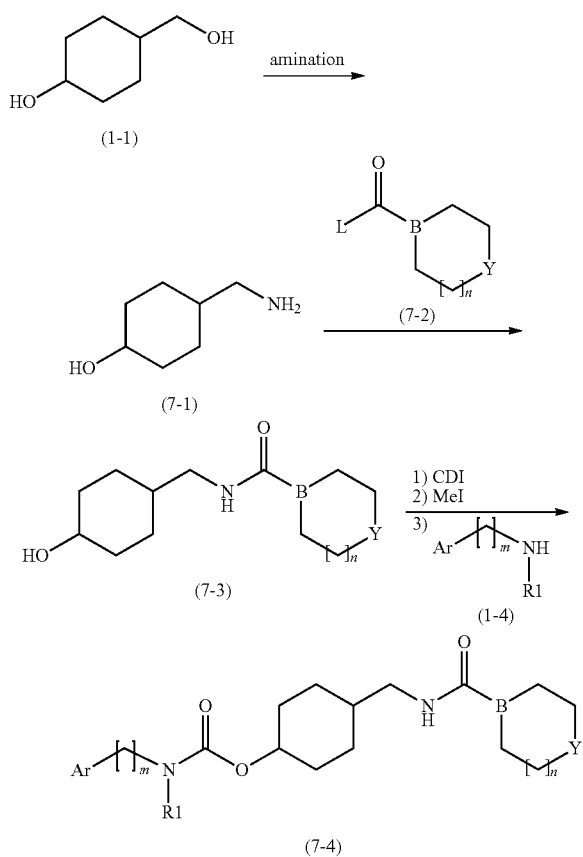

As illustrated in Reaction Scheme VII above, Compound (1-1) is reacted under amination conditions including, for example, Ms-Cl (mesyl chloride) and $NaN_3$, to obtain an intermediate, and Intermediate (7-1) may be synthesized therefrom by hydrogenation. Compound (7-1) is reacted with various carbonyl derivatives including a leaving group such as Cl (for example, Compound (7-2)) to synthesize Compound (7-3). Then, Compound (7-3) is reacted with CDI and methyl iodide, and then reacted with various amines (for example, Compound (1-4)) to obtain Compound (7-4).

Also, the methylcyclohexane derivative may include, in addition to the compound represented by Formula I above, a pharmaceutically acceptable salt thereof, that is, an acid or base additional salt thereof, and a stereochemical isomer of the compound represented by Formula I, and the pharmaceutically acceptable salt may be any one of various salts that allow a parent compound to maintain its activity in a subject that is to be administered with the compound and that do not cause adverse effects. The pharmaceutically acceptable salt may be an inorganic salt or an organic salt. Examples of an acid are acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzene sulfonic acid, benzoic acid, stearic acid, esylic acid, lactic acid, bicarbonic acid, biculfuric acid, bitartaric acid, oxalic acid, butylic acid, calcium edetic acid, camsylic acid, carbonic acid, chlorobenzoic acid, citric acid, idetic acid, toluene sulfonic acid, an edicylinic acid, ecylinic acid, fumaric acid, gluceptic acid, pamoic acid, gluconic acid, a glycolyl-larsanylic acid, methylnitric acid, a polygalatronic acid, hexyllisorcynonic acid, maloic acid, hydrobamic acid, hydrochlorinic acid, hydroiodoic acid, hydroxylnaphtholic acid, icethionic acid, lactobionic acid, mandelic acid, estolinic acid, mucic acid, a naphcylic acid, muconic acid, p-nitromethansulfonic acid, hexamic acid, pantothenic acid, monohydrogenphosphoric acid, dihydrogenphosphoric acid, salicylic acid, sulpamic acid, sulphanilic acid, methanesulfonic acid, and theoclic acid. Also, examples of a basic salt are an ammonium salt, and a salt of an alkali or alkali earth metal, such as lithium, sodium, potassium, magnesium, or calcium. Detailed examples of the basic salt are a salt containing an organic base, such as a benzathine, N-methyl-D-glucamine, or hydrabamine salt, and a salt containing an amino acid, such as arginine or lysine. Also, the salts may be converted into a free radical form by treatment with an appropriate base or acid. The term "additional salt" includes a solvent compound that is formed from the compound represented by Formula I and a salt thereof. Examples of the solvent compound are hydrates and alcoholates.

Also, the stereochemical isomer of the compound represented by Formula I according to an embodiment of the present invention refers to any compound that is obtainable from the compound represented by Formula I. If not defined or indicated otherwise, chemical appellations of compounds indicate any possible stereochemical isomer type mixtures, and examples of the mixture are diastereomers and enantiomers each having a basic molecular structure. In particular, a stereocenter may have an R- or S-coordination, and a substituent of 2-valent cyclic (partially) saturated radical may have cis- or trans-coordination. A compound having a double bond may have E or Z-stereochemistry in the double bond. The stereochemical isomer of the compound represented by Formula I is induced to be included in the scope of the present invention.

According to an embodiment of the present invention, the compound may have one of the following structures:

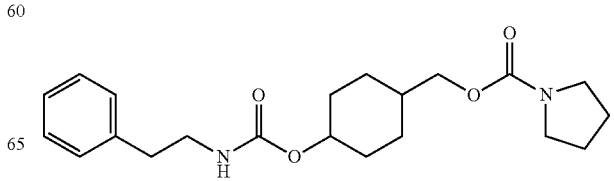

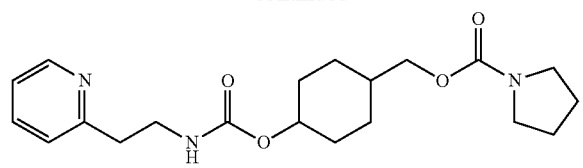 [SMILES: O=C(NCCc1ccccn1)OC1CCC(COC(=O)N2CCCC2)CC1]
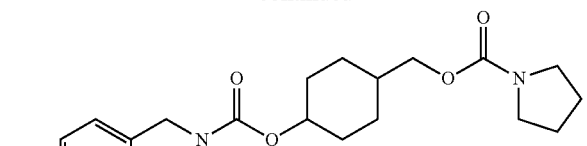
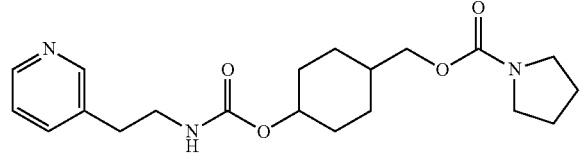 [SMILES: O=C(NCCc1cccnc1)OC1CCC(COC(=O)N2CCCC2)CC1]
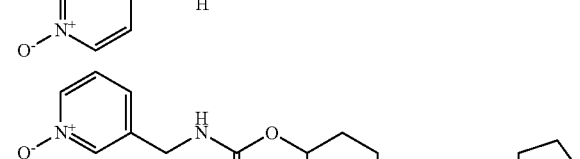
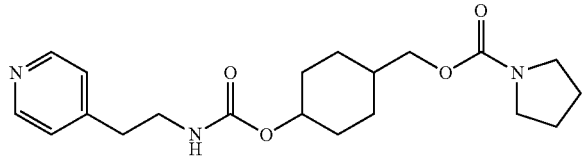 [SMILES: O=C(NCCc1ccncc1)OC1CCC(COC(=O)N2CCCC2)CC1]
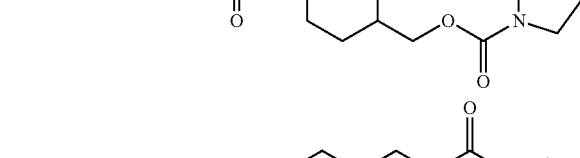
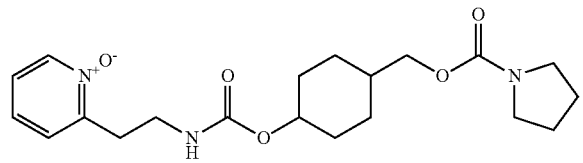
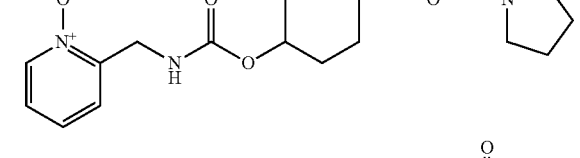
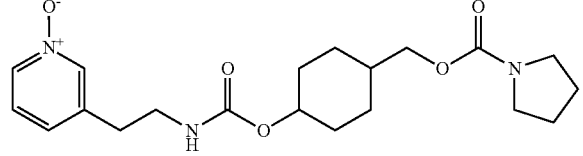
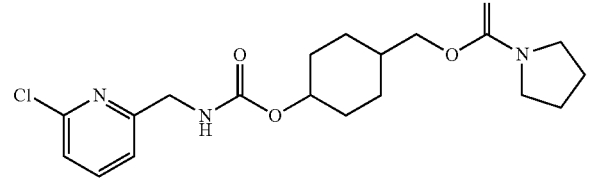
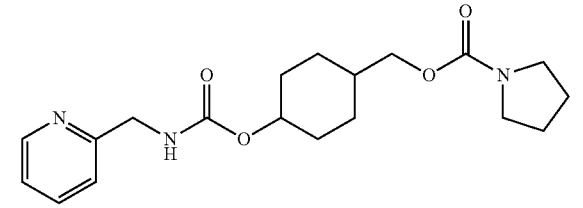
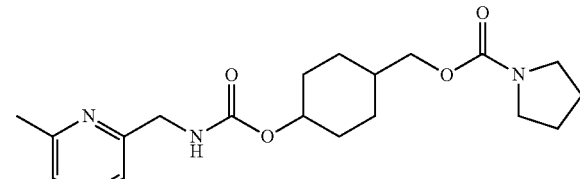
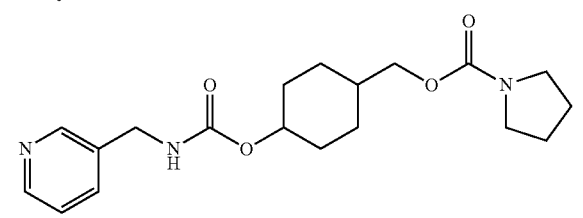
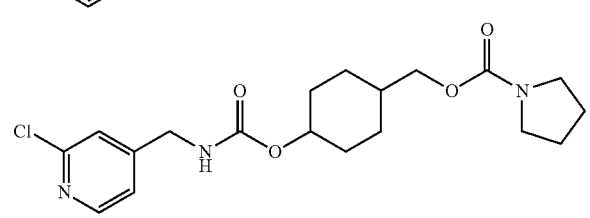
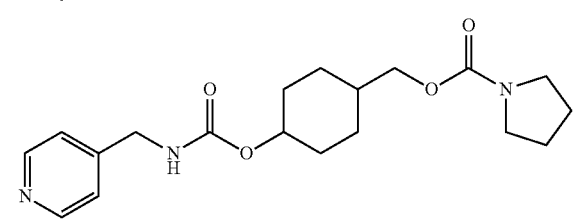
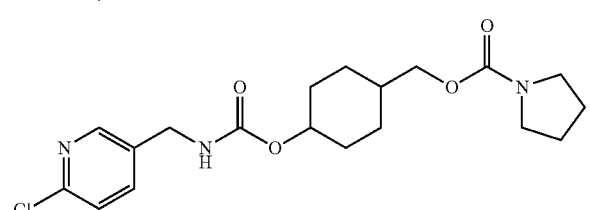
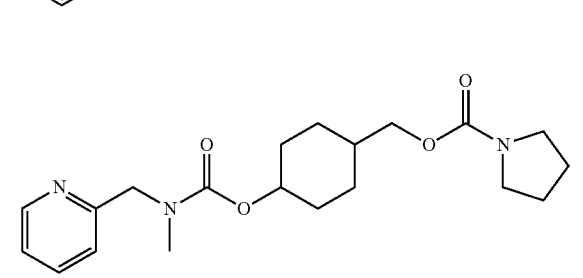
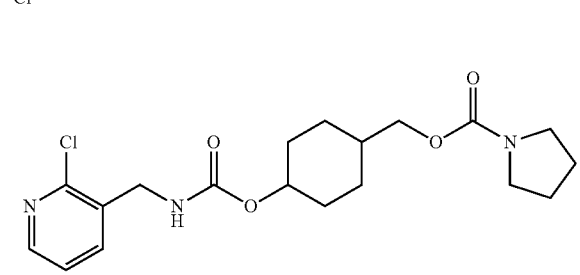

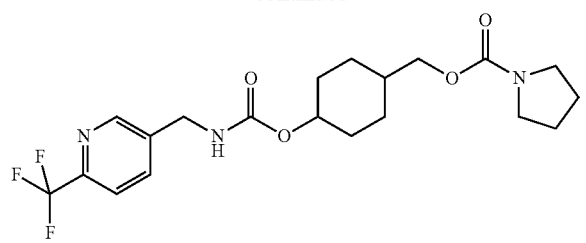
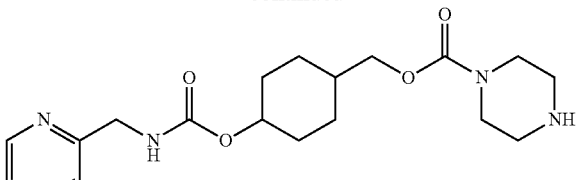
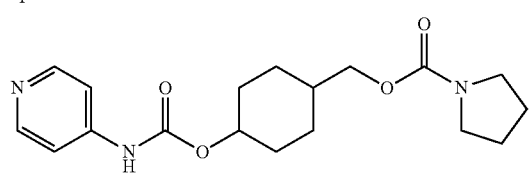
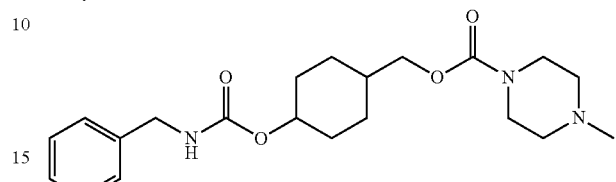
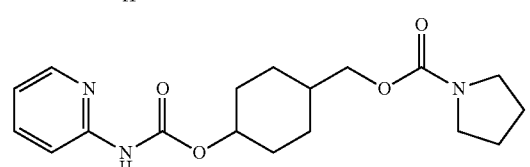
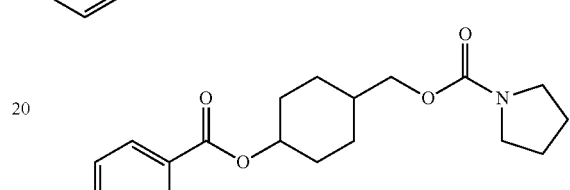
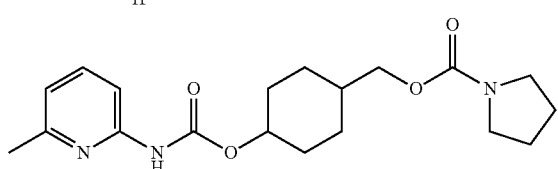
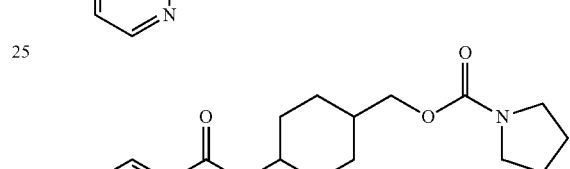
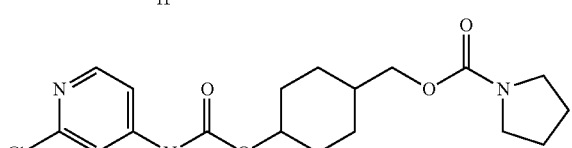
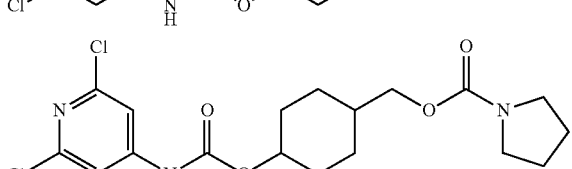
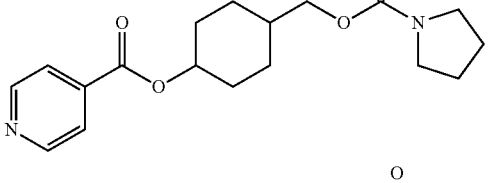
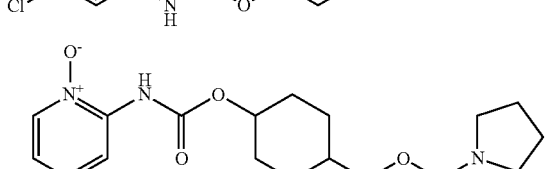
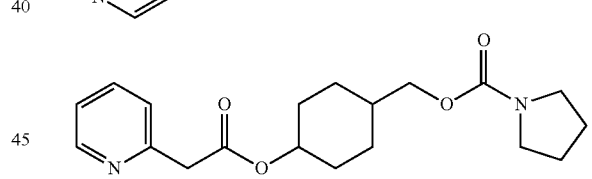
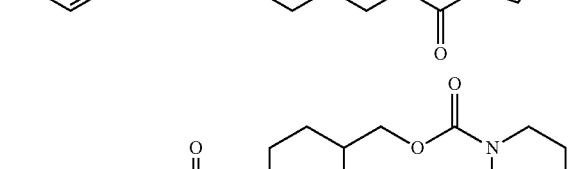
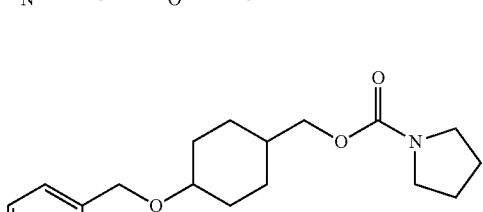
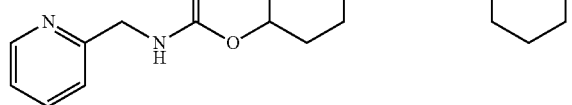
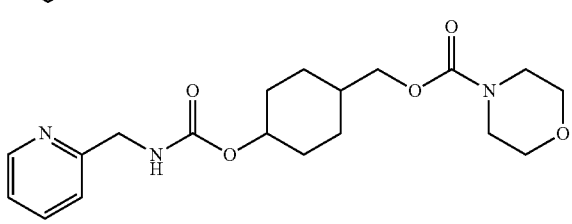
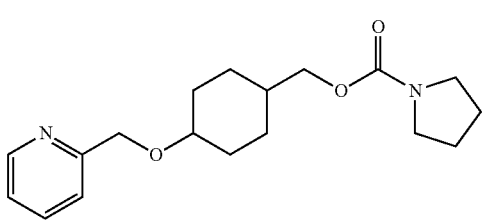

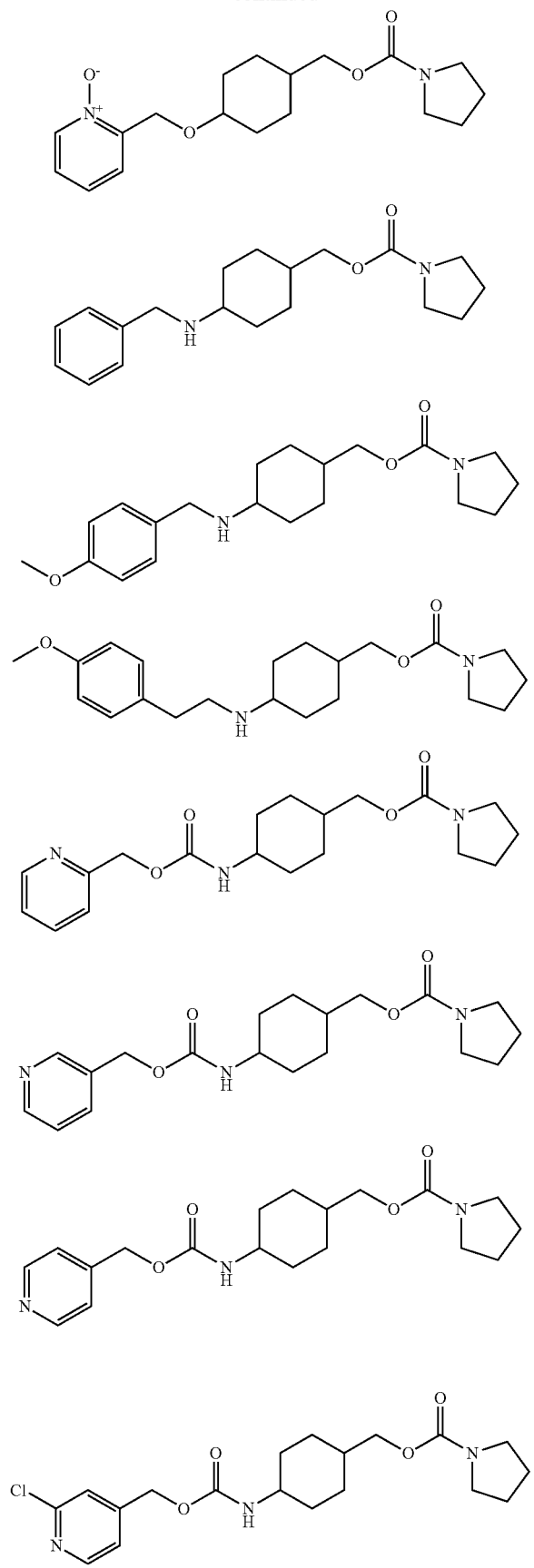
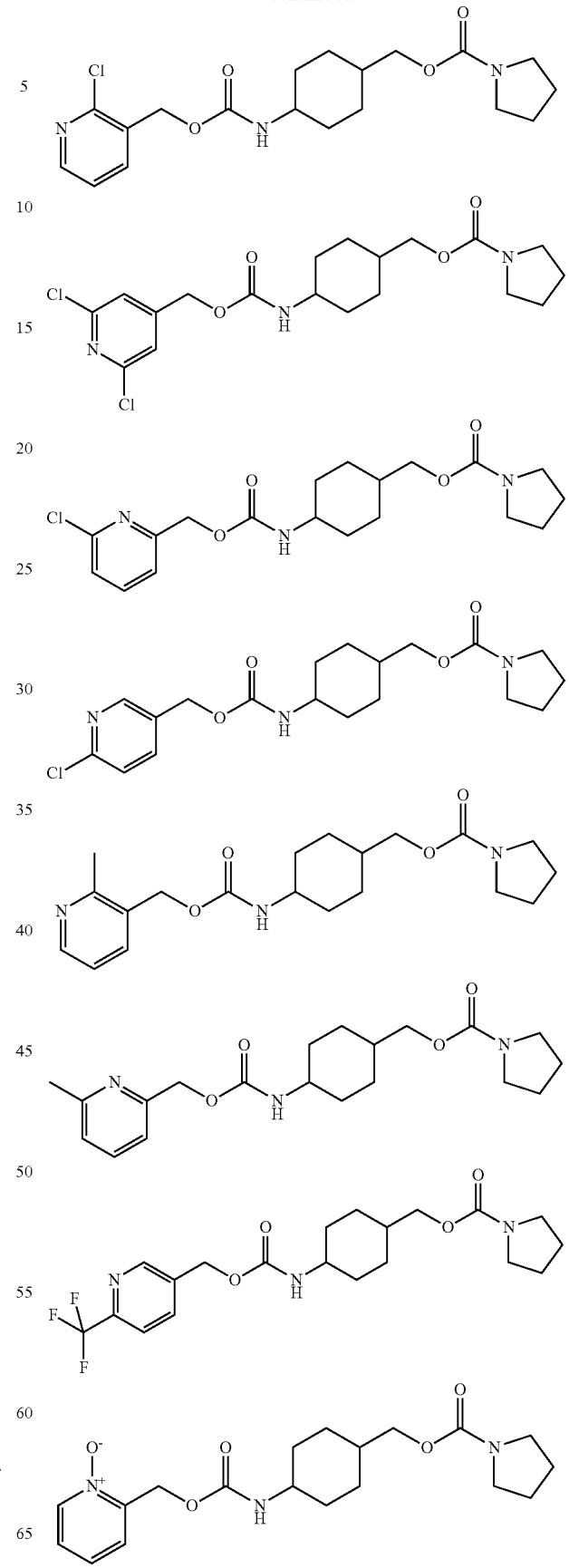

-continued

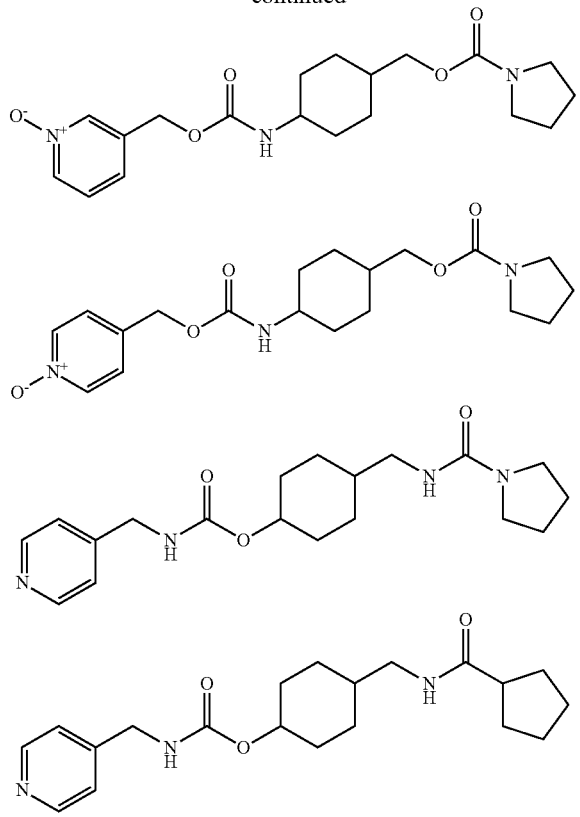

According to another aspect of the present invention, there is provided a pharmaceutical composition for the prevention or treatment of pain, wherein the pharmaceutical composition includes a therapeutically effective amount of the compound; and a pharmaceutically acceptable carrier.

The term "treatment" may be interpreted as prevention for the development of a disease, disorder, or state, suppression of a disease, disorder, or state, that is, suppression of the development thereof, and alleviation of a disease, disorder, or state, that is, induction of the regression of a disease, disorder, or state in an animal that is likely to have a disease, disorder, or state although it has not been diagnosed to have the a disease, disorder, or state. Accordingly, the term "therapeutically effective amount" refers to an amount that is sufficient to obtain a pharmaceutical effect, that is, a therapeutic effect.

The pharmaceutical composition according to an embodiment of the present invention may include the pharmaceutically acceptable carrier.

The pharmaceutically acceptable carrier of the pharmaceutical composition may be any one of various materials that are conventionally used in formulations, and non-limiting examples of the pharmaceutically acceptable carrier are lactose, dextrose, sucrose, sorbitol, mannitol, starch, acacia rubber, calcium phosphate, alginate, gelatin, calcium silicate, microcrystal cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition may further include a lubricant, a wetting agent, a flavoring agent, an emulsifier, a suspension agent, a preservative, etc. Suitable pharmaceutically acceptable carriers and formulations are disclosed in detail in *Remington's Pharmaceutical Sciences* (19th ed., 1995).

According to an embodiment of the present invention, the pharmaceutical composition may be orally or parenterally administered. The parenteral administration may be intravenous infusion, subcutaneous infusion, intramuscular infusion, intraperitoneal infusion, endothelium administration, topical administration, intranasal administration, intrapulmonary administration, or intrarectal administration. In the case of oral administration, an active material may be coated, or formulated to be protected from decomposition in a stomach. Also, the pharmaceutical composition may be administered via any device that allows an active material to reach a target cell.

A suitable administration amount of the pharmaceutical composition may differ according to a formation method, an administration method, age, weight, sex, and morbid state of a patient, food, an administration time, an administration pathway, an excretion rate, or reaction sensitivity. Typically, skilled physicians may determine and prescribe an administration amount that is effective for treatment or prevention without difficulty.

The pharmaceutical composition may be formulated in a unit dosage form by using a method that is obvious to one of ordinary kill in the art and a pharmaceutically acceptable carrier and/or an excipient, or may be prepared by using a multi-dosage container. In this case, the formulation may be a solution, suspension, or emulsion in an oil or aqueous medium, an extract, powder, granule, tablet, or capsule, and a dispersant or a stabilizer may be further included in the pharmaceutical composition.

The pharmaceutical composition may inhibit production of nitric oxide (NO) inside cells. An NO production inhibitor may alleviate symptoms of hyperalgesia and may function as a major target material with respect to various types of pain including inflammatory pain, nociceptive pain, and neuropathic pain. Accordingly, the pharmaceutical composition according to an embodiment of the present invention may be used in the prevention or treatment of pain. The pain may be acute pain or chronic pain, and may be, for example, cancer pain, labor pain, colic pain, neuropathic pain, postoperative pain, diabetic pain, post-herpetic pain, inflammatory disease pain, muscle pain, arthrodynia pain, a headache, or periodontal disease pain, such as gingivitis or paradentitis, but is not limited thereto.

According to another aspect of the present invention, there is provided a method of treating pain, wherein the method includes contacting the pharmaceutical composition and a subject.

The contacting may be performed in vitro or in vivo. If the contacting is performed in vivo, the method may further include administering the pharmaceutical composition to the subject.

The subject may be a cell, a tissue, an organ, or an individual. Also, the administration may involve directly contacting a solution of the pharmaceutical composition dissolved in an appropriate buffer solution and a cell, a tissue, or an organ, or may be parenteral administration. The pharmaceutical composition and administration method used in the treatment have already been described above and thus will not be described in detail herein.

The subject to which the pharmaceutical composition is administrable may be any kinds of animals. For example, the subject may be a human, or an animal, such as a dog, a cat, or a mouse.

BRIEF DESCRIPTION OF DRAWINGS

The above and other features and advantages of the present invention will become more apparent by describing in detail exemplary embodiments thereof with reference to the attached drawings in which:

FIG. 1 illustrates a view of the tail of a rat having a neuron damaged to induce neuropathic pain, wherein the damaged portion is marked.

MODE FOR THE INVENTION

The present invention will be described in further detail with reference to the following examples. These examples are for illustrative purposes only and are not intended to limit the scope of the present invention.

EXAMPLE 1

Synthesis of pyrrolidine-1-carboxylic acid 4-phenethylcarbamoyloxy-cyclohexylmethyl ester

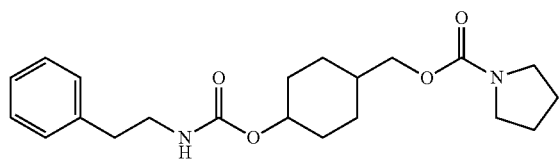

To a solution of 4-hydroxymethylcyclohexanol (2 mmol) in 10 mL of tetrahydrofuran (THF) was added CDI (2.2 mmol) and the resulting mixture was stirred for 2 hours at room temperature. Then, pyrrolidine (3 mmol) was added and stirred for 2 hours at 60° C. The reaction mixture was diluted with water, followed by few times of extraction with methylene chloride. The combined organic layer was dried over anhydrous magnesium sulfate, filtered and concentrated under reduced pressure. The residue was purified by column chromatography (silica gel, hexane:ethyl acetate=1:1) to provide a intermediate compound. The intermediate compound was dissolved in acetonitrile (10 mL), and CDI (2.2 mmol) was added. After 1 hour stirring at 80° C., methyl iodide (10 mmol) was added and stirred for additional 1 hour at 80° C. The resulting reaction mixture was concentrated under reduced pressure. The residue was dissolved in acetonitrile (10 mL), and phenethylamine (3 mmol) was added and stirred for 4 hours at 80° C. The reaction mixture was diluted with water, followed by few times of extraction with methylene chloride. The combined organic layer was dried over anhydrous magnesium sulfate, filtered and concentrated under reduced pressure. The residue was purified by column chromatography (silica gel, hexane:ethyl acetate=1:3), thereby completing the preparation of a target compound (411 mg, 55% yield).

$^1$H-NMR (300 MHz, CDCl$_3$), ppm (δ):7.36~7.15(m, 5H), 4.63~4.47(m, 2H), 3.90(d, 2H, J=6.3 Hz), 3.48~3.29(m, 6H), 2.81(t, 2H, J=6.3 Hz) 2.06~1.97(m, 2H), 1.90~1.76(m, 5H), 1.65~1.57(m, 2H), 1.35~1.09(m, 4H)

Examples 2 to 29 below were each performed in the same manner as Example 1, except that the used starting material was different from the starting material used in Example 1.

EXAMPLE 2

Synthesis of pyrrolidine-1-carboxylic acid 4-(2-pyridin-2-yl-ethylcarbamoyloxy)-cyclohexylmethyl ester

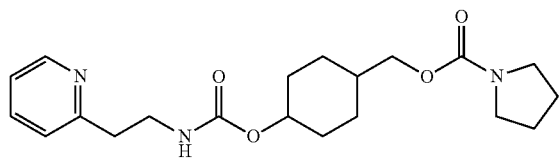

A target compound (375 mg, 50% yield) was obtained in the same manner as in Example 1, except that 2-pyridin-2-yl-ethylamine was used as a starting material.

$^1$H-NMR (300 MHz, CDCl$_3$), ppm (δ):8.55~8.51(m, 1H), 7.65~7.57(m, 1H), 7.19~7.11(m, 2H), 5.30(bs, 1H), 4.56~4.50(m, 1H), 3.90(d, 2H, J=6.1 Hz), 3.62~3.57(m, 2H), 3.40~3.31(m, 4H), 2.99(t, 2H, J=5.9 Hz), 2.06~1.50(m, 9H), 1.39~1.04(m, 4H)

EXAMPLE 3

Synthesis of pyrrolidine-1-carboxylic acid 4-(2-pyridin-3-yl-ethylcarbamoyloxy)-cyclohexylmethyl ester

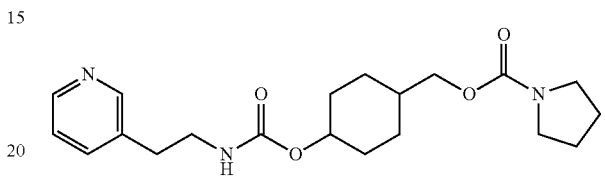

A target compound (338 mg, 45% yield) was obtained in the same manner as in Example 1, except that 2-pyridin-3-yl-ethylamine was used as a starting material.

$^1$H-NMR (300 MHz, CDCl$_3$), ppm (δ):8.51~8.43(m, 2H), 7.56~7.49(m, 1H), 7.25~7.20(m, 1H), 4.71~4.51(m, 2H), 3.90(d, 2H, J=6.3 Hz), 3.50~3.21(m, 6H), 2.82(t, 2H, J=6.6 Hz), 2.06~1.98(m, 2H), 1.93~1.75(m, 5H), 1.64~1.55(m, 2H), 1.37~1.13(m, 4H)

EXAMPLE 4

Synthesis of pyrrolidine-1-carboxylic acid 4-(2-pyridin-4-yl-ethylcarbamoyloxy)-cyclohexylmethyl ester

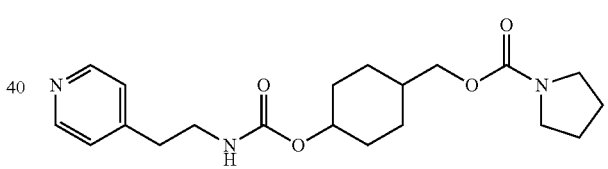

A target compound (390 mg, 52% yield) was obtained in the same manner as in Example 1, except that 2-pyridin-4-yl-ethylamine was used as a starting material.

$^1$H-NMR (300 MHz, CDCl$_3$), ppm (δ):8.56~8.48(m, 2H), 7.17~7.11(m, 2H), 4.74~4.49(m, 2H), 3.90(d, 2H, J=6.0 Hz), 3.51~3.29(m, 6H), 2.83(t, 2H, J=6.9 Hz), 2.08~1.99(m, 2H), 1.91~1.79(m, 5H), 1.65~1.56(m, 2H), 1.37~1.11(m, 4H)

EXAMPLE 5

Synthesis of pyrrolidine-1-carboxylic acid 4-[2-(1-oxy-pyridin-2-yl)-ethylcarbamoyloxy]-cyclohexylmethyl ester

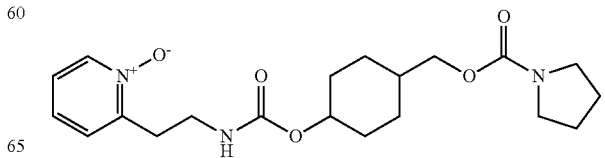

A target compound (313 mg, 40% yield) was obtained in the same manner as in Example 1, except that 2-(1-oxy-pyridin-2-yl)-ethylamine was used as a starting material.

$^1$H-NMR (300 MHz, CDCl$_3$), ppm (δ):8.27(d, 2H, J=6.0 Hz), 7.32~7.18(m, 3H), 5.74(bs, 1H), 4.57~4.50(m, 1H), 3.90(d, 2H, J=6.0 Hz), 3.63~3.53(m, 2H), 3.40~3.31(m, 4H), 3.18(t, 2H, J=6.3 Hz), 2.07~1.68(m, 8H), 1.65~1.55(m, 1H), 1.40~0.99(m, 4H)

EXAMPLE 6

Synthesis of pyrrolidine-1-carboxylic acid 4-[2-(1-oxy-pyridin-3-yl)-ethylcarbamoyloxy]-cyclohexylmethyl ester

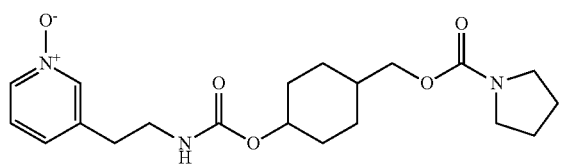 [SMILES: O=C(NCCc1ccc[n+]([O-])c1)OC1CCC(COC(=O)N2CCCC2)CC1]

A target compound (274 mg, 35% yield) was obtained in the same manner as in Example 1, except that 2-(1-oxy-pyridin-3-yl)-ethylamine was used as a starting material.

$^1$H-NMR (300 MHz, CDCl$_3$), ppm (δ):8.14~8.08(m, 2H), 7.29~7.12(m, 2H), 4.87(bs, 1H), 4.58~4.50(m, 1H), 3.90(d, 2H, J=6.3 Hz), 3.46~3.31(m, 6H), 2.80(t, 2H, J=6.3 Hz), 2.07~1.74(m, 8H), 1.66~1.57(m, 1H), 1.38~0.99(m, 4H)

EXAMPLE 7

Synthesis of pyrrolidine-1-carboxylic acid 4-(pyridin-2-ylmethylcarbamoyloxy)-cyclohexylmethyl ester

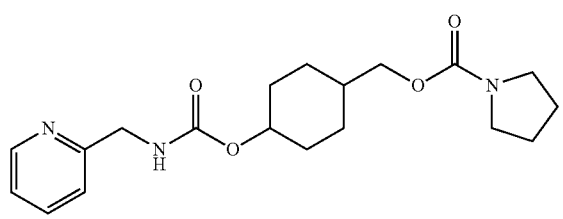 [SMILES: O=C(NCc1ccccn1)OC1CCC(COC(=O)N2CCCC2)CC1]

A target compound (448 mg, 62% yield) was obtained in the same manner as in Example 1, except that C-pyridin-2-yl-methylamine was used as a starting material.

$^1$H-NMR (500 MHz, CDCl$_3$), ppm (δ):8.38-8.37(d, 1H, J=6.3 Hz), 7.53-7.50(m, 1H), 7.16-7.15(d, 1H, J=6.3 Hz), 7.05-7.02(m, 1H), 6.16-6.14(m, 1H), 4.45(m, 1H), 4.34-4.33 (d, 2H, J=6.3 Hz), 3.76-3.75(d, 2H, J=6.3 Hz), 3.23-3.18(m, 4H), 1.93-1.91(m, 2H), 1.74-1.68(m, 6H), 1.48-1.47(m, 2H), 1.21-1.17(m, 2H), 1.02-0.97(m, 2H)

EXAMPLE 8

Synthesis of pyrrolidine-1-carboxylic acid 4-(pyridin-3-ylmethylcarbamoyloxy)-cyclohexylmethyl ester

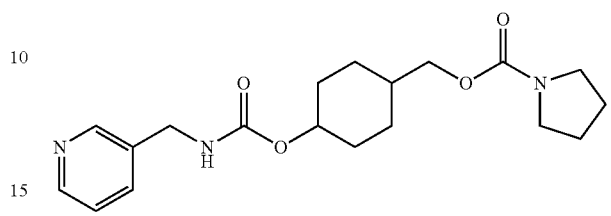

A target compound (470 mg, 65% yield) was obtained in the same manner as in Example 1, except that C-pyridin-3-yl-methylamine was used as a starting material.

$^1$H-NMR (300 MHz, CDCl$_3$), ppm (δ):8.55~8.49(m, 2H), 7.05(d, 1H, J=7.5 Hz), 7.30~7.22(m, 1H), 5.30(bs, 1H), 4.64~4.53(m, 1H), 4.37(d, 2H, J=6.3 Hz), 3.90(d, 2H, J=6.3 Hz), 3.41~3.29(m, 4H), 2.11~1.45(m, 9H), 1.39~1.06(m, 4H)

EXAMPLE 9

Synthesis of pyrrolidine-1-carboxylic acid 4-(pyridin-4-ylmethylcarbamoyloxy)-cyclohexylmethyl ester

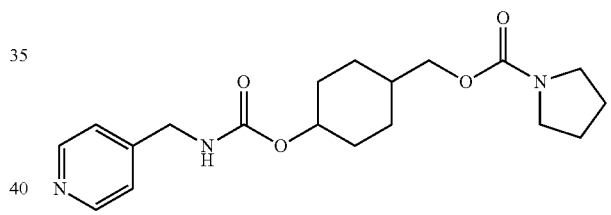

A target compound (405 mg, 56% yield) was obtained in the same manner as in Example 1, except that C-pyridin-4-yl-methylamine was used as a starting material.

$^1$H-NMR (300 MHz, CDCl$_3$), ppm (δ):8.54(d, 1H, J=6.0 Hz), 7.21(d, 1H, J=5.4 Hz), 5.39~5.15(m, 1H), 4.65~4.54(m, 1H), 4.38(d, 2H, J=6.3 Hz), 3.90(d, 2H, J=6.3 Hz), 3.49~3.29 (m, 4H), 2.16~1.47(m, 9H), 1.41~1.05(m, 4H)

EXAMPLE 10

Synthesis of pyrrolidine-1-carboxylic acid 4-(methyl-pyridin-2-ylmethyl-carbamoyloxy)-cyclohexylmethyl ester

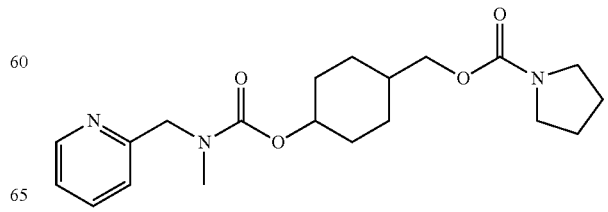

A target compound (248 mg, 33% yield) was obtained in the same manner as in Example 1, except that N-methyl-N-(2-pyridinylmethyl)amine was used as a starting material.

$^1$H-NMR (300 MHz, CDCl$_3$), ppm (δ):8.55(d, 1H, J=4.2 Hz), 7.71~7.63(m, 1H), 7.30~7.15(m, 2H), 4.69~4.50(m, 3H), 3.91(s, 2H), 3.40~3.23(m, 4H), 3.01~2.91(m, 3H), 2.11~1.51(m, 9H), 1.42~1.05(m, 4H)

EXAMPLE 11

Synthesis of pyrrolidine-1-carboxylic acid 4-(1-oxy-pyridin-4-ylmethylcarbamoyloxy)-cyclohexylmethyl ester

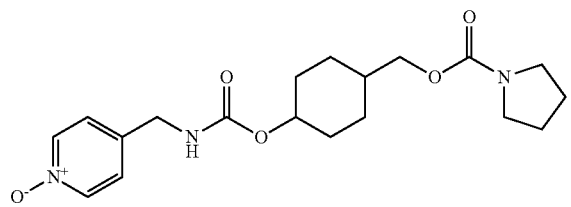 [SMILES: O=C(NCc1cc[n+]([O-])cc1)OC1CCC(COC(=O)N2CCCC2)CC1]

A target compound (393 mg, 52% yield) was obtained in the same manner as in Example 1, except that C-(1-oxy-pyridin-4-yl)-methylamine was used as a starting material.

$^1$H-NMR (500 MHz, CDCl$_3$), ppm (δ):8.14-8.13(d, 2H, J=6.3 Hz), 7.29-7.21(d, 2H, J=6.3 Hz), 5.95(s, 1H), 4.58-4.52(m, 1H), 3.91-3.85(m, 2H), 3.36-3.30(m, 5H), 3.00-2.50(m, 1H), 2.0(m, 2H), 1.83-1.82(m, 7H), 1.59-1.53(m, 2H), 1.31-1.21(m, 4H), 1.14-1.03(m, 2H)

EXAMPLE 12

Synthesis of pyrrolidine-1-carboxylic acid 4-(1-oxy-pyridin-3-ylmethylcarbamoyloxy)-cyclohexylmethyl ester

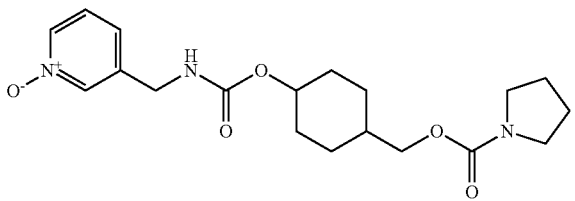 [SMILES: O=C(NCc1ccc[n+]([O-])c1)OC1CCC(COC(=O)N2CCCC2)CC1]

A target compound (325 mg, 43% yield) was obtained in the same manner as in Example 1, except that C-(1-oxy-pyridin-3-yl)-methylamine was used as a starting material.

$^1$H-NMR (500 MHz, CDCl$_3$), ppm (δ):8.21-8.13(m, 1H), 7.26-7.24(m, 3H), 5.16-4.59(m, 1H), 4.35(m, 1H), 3.92-3.91(m, 1H), 3.41-3.33(m, 2H), 2.08-2.04(m, 1H), 1.87-1.84(m, 4H), 1.63(m, 4H), 1.35-1.11(m, 2H)

EXAMPLE 13

Synthesis of pyrrolidine-1-carboxylic acid 4-(1-oxy-pyridin-2-ylmethylcarbamoyloxy)-cyclohexylmethyl ester

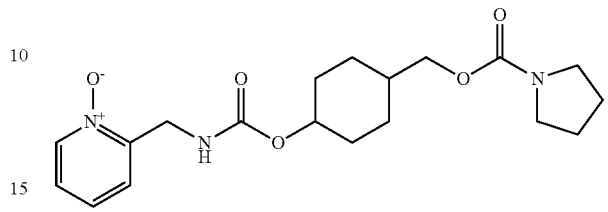

A target compound (264 mg, 35% yield) was obtained in the same manner as in Example 1, except that C-(1-oxy-pyridin-2-yl)-methylamine was used as a starting material.

$^1$H-NMR (500 MHz, CDCl$_3$), ppm (δ):8.29-8.19(d, 1H, J=6.3 Hz), 7.38-7.37(m, 1H), 7.25-7.18(m, 2H), 6.23-6.21(m, 1H), 4.48-4.45(m, 3H), 3.85-3.82(m, 2H), 3.32-3.253.25(m, 4H), 1.97-1.93(m, 2H), 1.81-1.74(m, 6H), 1.58-1.82(m, 2H), 1.27-1.20(m, 4H)

EXAMPLE 14

Synthesis of pyrrolidine-1-carboxylic acid 4-(6-chloro-pyridin-2-ylmethylcarbamoyloxy)-cyclohexylmethyl ester

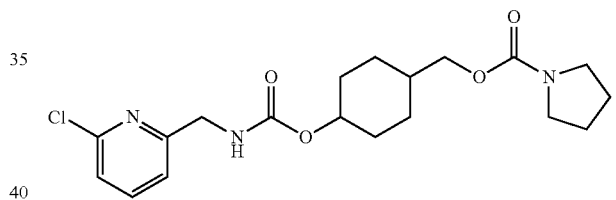

A target compound (491 mg, 62% yield) was obtained in the same manner as in Example 1, except that C-(6-chloro-pyridin-2-yl)-methylamine was used as a starting material.

$^1$H-NMR (300 MHz, CDCl$_3$), ppm (δ):7.67~7.60(m, 1H), 7.26~7.21(m, 2H), 5.61~5.55(m, 1H), 4.64~4.53(m, 1H), 4.44(d, 2H, J=5.7 Hz), 3.90(d, 2H, J=6.0 Hz), 3.42~3.28(m, 4H), 2.10~1.99(m, 2H), 1.92~1.84(m, 5H), 1.67~1.55(m, 2H), 1.40~1.03(m, 4H)

EXAMPLE 15

Synthesis of pyrrolidine-1-carboxylic acid 4-(6-methyl-pyridin-2-ylmethylcarbamoyloxy)-cyclohexylmethyl ester

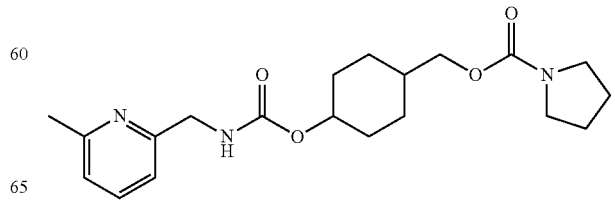

A target compound (451 mg, 60% yield) was obtained in the same manner as in Example 1, except that C-(6-methyl-pyridin-2-yl)-methylamine was used as a starting material.

¹H-NMR (300 MHz, CDCl₃), ppm (δ):7.58~7.50(m, 1H), 7.10~7.01(m, 2H), 5.84~5.79(m, 1H), 4.65~4.55(m, 1H), 4.44(d, 2H, J=5.1 Hz), 3.90(d, 2H, J=6.3 Hz), 3.42~3.10(m, 4H), 2.53(s, 3H), 2.15~1.99(m, 2H), 1.95~1.75(m, 5H), 1.73~1.52(m, 2H), 1.44~1.03(m, 4H)

EXAMPLE 16

Synthesis of pyrrolidine-1-carboxylic acid 4-(2-chloro-pyridin-4-ylmethylcarbamoyloxy)-cyclohexylmethyl ester

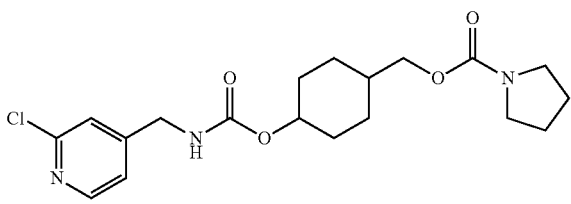 [SMILES: O=C(NCc1ccnc(Cl)c1)OC1CCC(COC(=O)N2CCCC2)CC1]

A target compound (523 mg, 66% yield) was obtained in the same manner as in Example 1, except that C-(2-chloro-pyridin-4-yl)-methylamine was used as a starting material.

¹H-NMR (300 MHz, CDCl₃), ppm (δ):8.33(d, 1H, J=5.1 Hz), 7.25(s, 1H), 7.14(d, 1H, J=4.8 Hz), 5.33~5.26(m, 1H), 4.65~4.54(m, 1H), 4.36(d, 2H, J=6.3 Hz), 3.90(d, 2H, J=6.3 Hz), 3.41~3.29(m, 4H), 2.18~1.99(m, 2H), 1.95~1.77(m, 6H), 1.70~1.52(m, 1H), 1.43~1.03(m, 4H)

EXAMPLE 17

Synthesis of pyrrolidine-1-carboxylic acid 4-(6-chloro-pyridin-3-ylmethylcarbamoyloxy)-cyclohexylmethyl ester

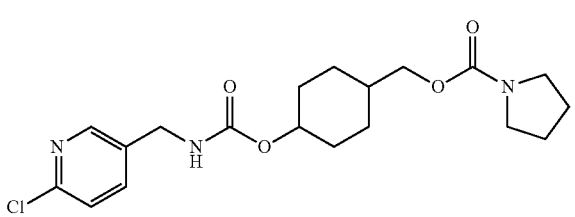 [SMILES: O=C(NCc1ccc(Cl)nc1)OC1CCC(COC(=O)N2CCCC2)CC1]

A target compound (435 mg, 55% yield) was obtained in the same manner as in Example 1, except that C-(6-chloro-pyridin-3-yl)-methylamine was used as a starting material.

¹H-NMR (300 MHz, CDCl₃), ppm (δ):8.31(s, 1H), 7.63(d, 1H, J=7.2 Hz), 7.30(d, 1H, J=8.4 Hz), 5.20~5.12(m, 1H), 4.63~4.52(m, 1H), 4.34(d, 2H, J=6.0 Hz), 3.90(d, 2H, J=6.6 Hz), 3.41~3.28(m, 4H), 2.13~1.99(m, 2H), 1.97~1.72(m, 6H), 1.69~1.53(m, 1H), 1.42~1.04(m, 4H)

EXAMPLE 18

Synthesis of pyrrolidine-1-carboxylic acid 4-(2-chloro-pyridin-3-ylmethylcarbamoyloxy)-cyclohexylmethyl ester

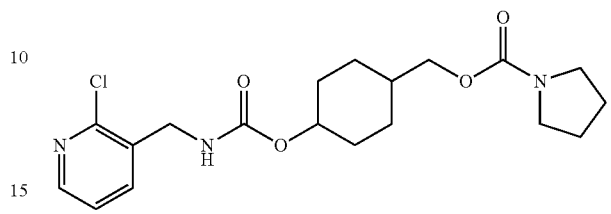

A target compound (404 mg, 51% yield) was obtained in the same manner as in Example 1, except that C-(2-chloro-pyridin-3-yl)-methylamine was used as a starting material.

¹H-NMR (300 MHz, CDCl₃), ppm (δ):8.34~8.28(m, 1H), 7.75(d, 1H, J=6.6 Hz), 7.27~7.21(m, 1H), 5.35~5.27(m, 1H), 4.62~4.50(m, 1H), 4.42(d, 2H, J=6.6 Hz), 3.90(d, 2H, J=6.3 Hz), 3.42~3.28(m, 4H), 2.15~1.77(m, 8H), 1.74~1.50(m, 1H), 1.46~1.02(m, 4H)

EXAMPLE 19

Synthesis of pyrrolidine-1-carboxylic acid 4-(6-trifluoromethyl-pyridin-3-ylmethylcarbamoyloxy)-cyclohexylmethyl ester

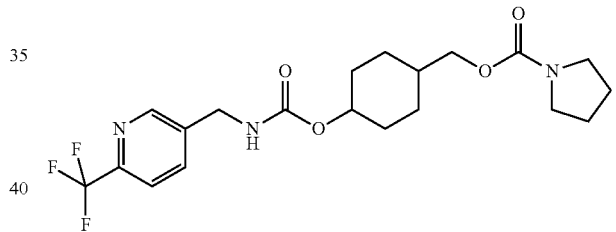

A target compound (490 mg, 57% yield) was obtained in the same manner as in Example 1, except that C-(6-trifluoromethyl-pyridin-3-yl)-methylamine was used as a starting material.

¹H-NMR (300 MHz, CDCl₃), ppm (δ):8.66(s, 1H), 7.84(d, 1H, J=8.4 Hz), 7.66(d, 1H, J=8.1 Hz), 5.23~5.15(m, 1H), 4.64~4.54(m, 1H), 4.45(d, 2H, J=6.3 Hz), 3.90(d, 2H, J=6.3 Hz), 3.43~3.27(m, 4H), 2.17~1.99(m, 2H), 1.95~1.76(m, 5H), 1.74~1.57(m, 2H), 1.40~1.02(m, 4H)

EXAMPLE 20

Synthesis of pyrrolidine-1-carboxylic acid 4-(pyridin-4-ylcarbamoyloxy)-cyclohexylmethyl ester

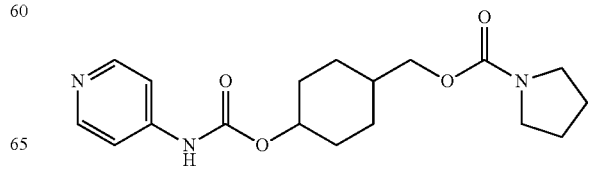

A target compound (208 mg, 30% yield) was obtained in the same manner as in Example 1, except that pyridin-4-ylamine was used as a starting material.

¹H-NMR (300 MHz, CDCl₃), ppm (δ):8.45(d, 2H, J=5.7 Hz), 7.50(s, 1H), 7.37(d, 2H, J=5.4 Hz), 4.75~4.63(m, 1H), 3.93(d, 2H, J=6.3 Hz), 3.43~3.30(m, 4H), 2.19~2.03(m, 2H), 1.99~1.80(m, 6H), 1.77~1.60(m, 1H), 1.49~1.27(m, 2H), 1.25~1.10(m, 2H)

EXAMPLE 21

Synthesis of pyrrolidine-1-carboxylic acid 4-(pyridin-2-ylcarbamoyloxy)-cyclohexylmethyl ester

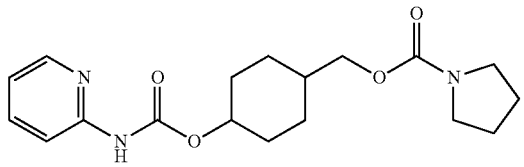 [SMILES: O=C(Nc1ccccn1)OC1CCC(COC(=O)N2CCCC2)CC1]

A target compound (174 mg, 25% yield) was obtained in the same manner as in Example 1, except that pyridin-2-ylamine was used as a starting material.

¹H-NMR (300 MHz, CDCl₃), ppm (δ):8.67(s, 1H), 8.33~8.27(m, 2H), 7.99(d, 1H, J=8.1 Hz), 7.72~7.65(m, 1H), 7.01~6.94(m, 1H), 4.79~4.63(m, 1H), 3.93(d, 2H, J=6.3 Hz), 3.44~3.28(m, 4H), 2.19~1.57(m, 9H), 1.50~1.10(m, 4H)

EXAMPLE 22

Synthesis of pyrrolidine-1-carboxylic acid 4-(6-methyl-pyridin-2-ylcarbamoyloxy)-cyclohexylmethyl ester

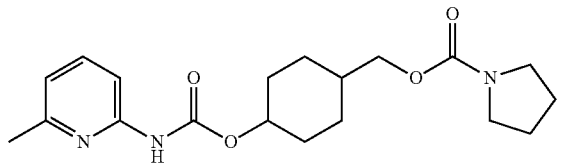 [SMILES: Cc1cccc(NC(=O)OC2CCC(COC(=O)N3CCCC3)CC2)n1]

A target compound (166 mg, 23% yield) was obtained in the same manner as in Example 1, except that 6-methyl-pyridin-2-ylamine was used as a starting material.

¹H-NMR (300 MHz, CDCl₃), ppm (δ):7.73(d, 1H, J=8.1 Hz), 7.60~7.52(m, 2H), 6.83(d, 1H, J=7.2 Hz), 4.71~4.62(m, 1H), 3.95~3.90(m, 2H), 3.47~3.28(m, 4H), 2.44(s, 3H), 2.19~1.54(m, 9H), 1.49~1.08(m, 4H)

EXAMPLE 23

Synthesis of pyrrolidine-1-carboxylic acid 4-(2-chloro-pyridin-4-ylcarbamoyloxy)-cyclohexylmethyl ester

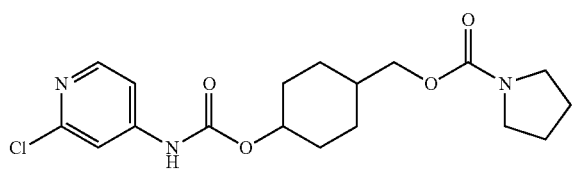 [SMILES: O=C(Nc1ccnc(Cl)c1)OC1CCC(COC(=O)N2CCCC2)CC1]

A target compound (206 mg, 27% yield) was obtained in the same manner as in Example 1, except that 2-chloro-pyridin-4-ylamine was used as a starting material.

¹H-NMR (300 MHz, CDCl₃), ppm (δ):8.21(d, 1H, J=5.4 Hz), 7.49(s, 1H), 7.23(d, 1H, J=5.7 Hz), 7.09(s, 1H), 4.74~4.63(m, 1H), 3.91(d, 2H, J=5.7 Hz), 3.42~3.29(m, 4H), 2.18~2.03(m, 2H), 1.95~1.80(m, 5H), 1.49~1.12(m, 6H)

EXAMPLE 24

Synthesis of pyrrolidine-1-carboxylic acid 4-(2,6-dichloro-pyridin-4-ylcarbamoyloxy)-cyclohexylmethyl ester

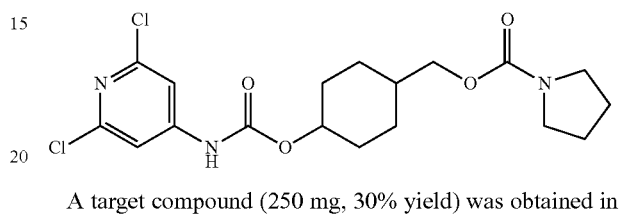

A target compound (250 mg, 30% yield) was obtained in the same manner as in Example 1, except that 2,6-dichloro-pyridin-4-ylamine was used as a starting material.

¹H-NMR (300 MHz, CDCl₃), ppm (δ):7.80(s, 1H), 7.45(s, 2H), 5.01(s, 1H), 3.94(d, 2H, J=6.6 Hz), 3.41~3.34(m, 4H), 1.97~1.70(m, 7H), 1.65~1.55(m, 4H), 1.38~1.10(m, 2H)

EXAMPLE 25

Synthesis of pyrrolidine-1-carboxylic acid 4-(1-oxy-pyridin-2-ylcarbamoyloxy)-cyclohexylmethyl ester

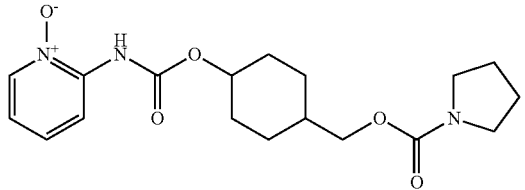 [SMILES: O=C(Nc1cccc[n+]1[O-])OC1CCC(COC(=O)N2CCCC2)CC1]

A target compound (225 mg, 31% yield) was obtained in the same manner as in Example 1, except that 1-oxy-pyridin-2-ylamine was used as a starting material.

¹H-NMR (500 MHz, CDCl₃), ppm (δ):9.40(s, 1H), 8.22-8.21(m, 1H), 8.17-8.15(m, 1H), 7.34-7.30(m, 1H), 6.95-6.92(m, 1H), 4.73-4.69(m, 1H), 3.93-3.89(m, 2H), 3.40-3.32(m, 5H), 2.12-2.09(m, 2H), 1.89-1.85(m, 8H), 1.68-1.65(m, 2H), 1.46-1.41(m, 3H), 1.21-1.13(m, 3H)

EXAMPLE 26

Synthesis of piperidine-1-carboxylic acid 4-benzylcarbamoyloxy-cyclohexylmethyl ester

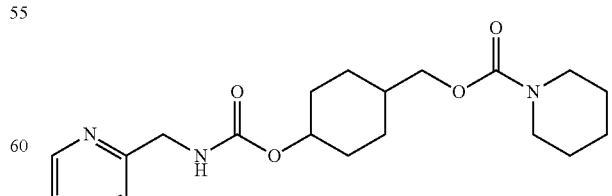

A target compound (488 mg, 65% yield) was obtained in the same manner as in Example 1, except that C-pyridin-2-yl-methylamine and piperidine was used as a starting material.

¹H-NMR (500 MHz, CDCl₃), ppm (δ):8.58-8.53(m, 1H), 7.70-7.63(m, 1H), 7.30-7.25(m, 1H), 7.23-7.16(m, 1H), 5.74 (bs, 1H), 4.96(s, 1H), 4.51-4.45(m, 2H), 3.93(d, 2H, J=6.6 Hz), 3.43-3.37(m, 4H), 1.97-1.88(m, 2H), 1.78-1.67(m, 1H), 1.62-1.49(m, 10H), 1.43-1.33(m, 2H)

EXAMPLE 27

Synthesis of morpholine-4-carboxylic acid 4-benzylcarbamoyloxy-cyclohexylmethyl ester

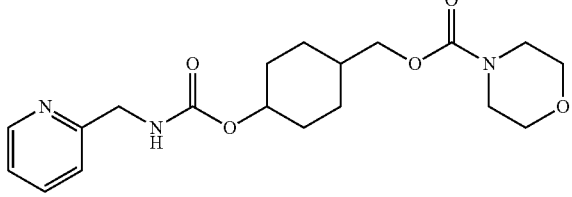

A target compound (498 mg, 66% yield) was obtained in the same manner as in Example 1, except that C-pyridin-2-yl-methylamine and morpholine were used as starting materials.

¹H-NMR (500 MHz, CDCl₃), ppm (δ):8.58-8.53(m, 1H), 7.70-7.63(m, 1H), 7.30-7.25(m, 1H), 7.21-7.16(m, 1H), 5.75 (bs, 1H), 4.97(s, 1H), 4.51-4.45(m, 2H), 3.99-3.91(m, 2H), 3.72-3.63(m, 4H), 3.51-3.43(m, 4H), 1.98-1.88(m, 2H), 1.78-1.67(m, 1H), 1.62-1.52(m, 4H), 1.44-1.33(m, 2H)

EXAMPLE 28

Synthesis of piperazine-1-carboxylic acid 4-benzylcarbamoyloxy-cyclohexylmethyl ester HCl salt

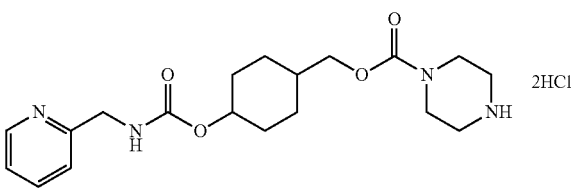 [SMILES: O=C(NCc1ccccn1)OC1CCC(COC(=O)N2CCNCC2)CC1]

A Boc-protected target compound was obtained in the same manner as in Example 1, except that C-pyridin-2-yl-methylamine and 1-Boc-piperazine were used as starting materials. The obtained compound was dissolved with methylene chloride and then a saturated HCl solution in ether was added. The reaction mixture was concentrated under reduced pressure, thereby completing the preparation of a target compound (279 mg, 31% yield).

¹H-NMR (500 MHz, DMSO-d₆), ppm (δ):9.03(s, 2H), 8.61 (s, 1H), 8.07(s, 1H), 7.77(s, 1H), 7.51(s, 1H), 4.44-4.37 (m, 4H), 3.86-3.85(m, 3H), 3.07(s, 6H), 1.96-1.94(m, 2H), 1.76-1.73(m, 2H), 1.58 (s, 1H), 1.32-1.27(m, 2H), 1.10-1.08 (m, 2H)

EXAMPLE 29

Synthesis of 4-methyl-piperazine-1-carboxylic acid 4-benzylcarbamoyloxy-cyclohexylmethyl ester

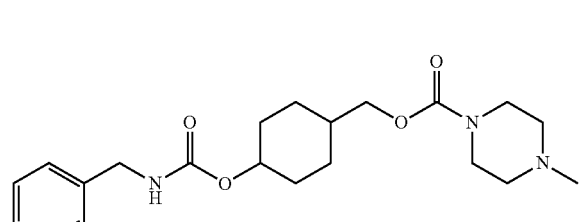

A target compound (101 mg, 13% yield) was obtained in the same manner as in Example 1, except that benzylamine and 1-methyl-piperazine were used as starting materials and methyl iodide was not used at the second step.

¹H-NMR (500 MHz, CDCl₃), ppm (δ):7.38~7.24(m, 5H), 4.96(bs, 1H), 4.65~4.54(m, 1H), 3.92(d, 2H, J=6.4 Hz), 3.51~3.47(m, 4H), 2.41~2.34(m, 4H), 2.30(s, 3H), 2.12~2.02 (m, 1H), 1.94~1.79(m, 2H), 1.68~1.52(m, 2H), 1.38~1.29(m, 2H), 1.20~1.09(m, 2H)

EXAMPLE 30

Synthesis of pyridine-2-carboxylic acid 4-(pyrrolidine-1-carbonyloxymethyl)-cyclohexyl ester

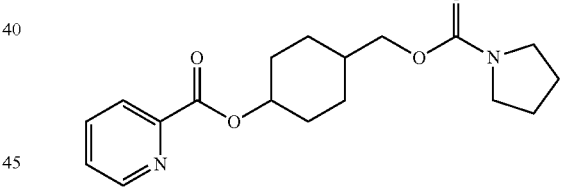

To a solution of pyrrolidine-1-carboxylic acid 4-hydroxy-cyclohexylmethyl ester (1 mmol) in methylene chloride (5 mL) were added picolinoyl chloride (1.1 mmol) and triethylamine (1.5 mmol) and the resulting mixture was stirred for 16 hours at room temperature. The reaction mixture was diluted with water, followed by few times of extraction with methylene chloride. The combined organic layer was dried over anhydrous magnesium sulfate, filtered and concentrated under reduced pressure. The residue was purified by column chromatography (silica gel, ethyl acetate), thereby completing the preparation of a target compound (233 mg, 70% yield).

¹H-NMR (300 MHz, CDCl₃), ppm (δ):8.80~8.76(m, 1H), 8.15~8.11(m, 1H), 7.90~7.80(m, 1H), 7.50~7.45(m, 1H), 5.08~4.98(m, 1H), 3.98(d, 2H, J=6.6 Hz), 3.43~3.33(m, 4H), 2.17~2.08(m, 2H), 1.99~1.83(m, 5H), 1.81~1.53(m, 3H), 1.20~1.08(m, 3H)

Examples 31 to 33 below were each performed in the same manner as Example 30, except that the used starting material was different from the starting material used in Example 30.

EXAMPLE 31

Synthesis of pyridine-3-carboxylic acid 4-(pyrrolidine-1-carbonyloxymethyl)-cyclohexyl ester

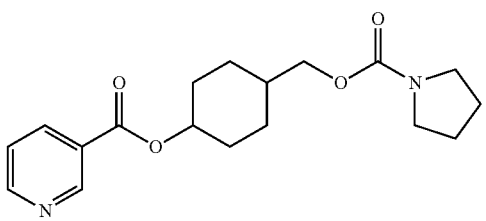 [SMILES: O=C(OC1CCC(COC(=O)N2CCCC2)CC1)c1cccnc1]

A target compound (316 mg, 65% yield) was prepared in the same manner as in Example 30, except that nicotinoyl chloride was used as a starting material.

¹H-NMR (300 MHz, CDCl₃), ppm (δ):9.22(d, 1H, J=2.1 Hz), 8.78~8.76(m, 1H), 8.32~8.28(m, 1H), 7.42~7.37(m, 1H), 5.00~4.93(m, 1H), 3.95(d, 2H, J=6.3 Hz), 3.44~3.32(m, 4H), 2.20~2.11(m, 2H), 1.99~1.84(m, 6H), 1.75~1.71(m, 1H), 1.60~1.47(m, 2H), 1.30~1.18(m, 2H)

EXAMPLE 32

Synthesis of pyridine-4-carboxylic acid 4-(pyrrolidine-1-carbonyloxymethyl)-cyclohexyl ester

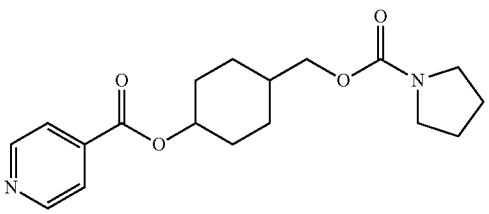 [SMILES: O=C(OC1CCC(COC(=O)N2CCCC2)CC1)c1ccncc1]

A target compound (223 mg, 67% yield) was prepared in the same manner as in Example 30, except that isonicotinoyl chloride was used as a starting material.

¹H-NMR (300 MHz, CDCl₃), ppm (δ):8.79~8.75(m, 2H), 7.87~7.82(m, 2H), 5.02~4.89(m, 1H), 3.95(d, 2H, J=6.6 Hz), 3.44~3.32(m, 4H), 2.25~2.02(m, 2H), 1.99~1.80(m, 6H), 1.78~1.60(m, 1H), 1.58~1.47(m, 2H), 1.40~1.10(m, 2H)

EXAMPLE 33

Synthesis of pyrrolidine-1-carboxylic acid 4-(2-pyridin-2-yl-acetoxy)-cyclohexylmethyl ester

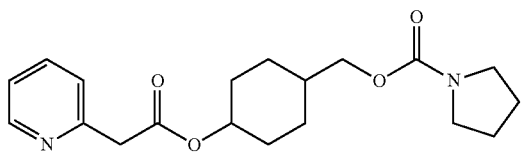 [SMILES: O=C(Cc1ccccn1)OC1CCC(COC(=O)N2CCCC2)CC1]

A target compound (204 mg, 59% yield) was prepared in the same manner as in Example 30, except that pyridin-2-yl-acetyl chloride was used as a starting material.

¹H-NMR (300 MHz, CDCl₃), ppm (δ):8.58~8.53(m, 1H), 7.70~7.61(m, 1H), 7.29(d, 1H, J=7.8 Hz), 7.22~7.16(m, 1H), 4.78~4.68(m, 1H), 3.91~3.81(m, 4H), 3.41~3.29(m, 4H), 2.05~1.98(m, 2H), 1.90~1.76(m, 5H), 1.73~1.51(m, 2H), 1.46~1.12(m, 4H)

EXAMPLE 34

Synthesis of pyrrolidine-1-carboxylic acid 4-benzyloxy-cyclohexylmethyl ester

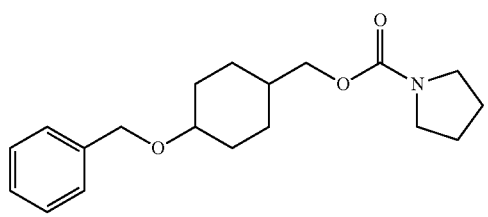 [SMILES: O=C(OCC1CCC(OCc2ccccc2)CC1)N1CCCC1]

To a solution of pyrrolidine-1-carboxylic acid 4-hydroxy-cyclohexyl methyl ester (1 mmol) in DMF (5 mL) were added sodium hydride (1 mmol) and benzyl bromide (1 mmol) and the resulting mixture was stirred for 16 hours at 60° C. The reaction mixture was diluted with water, followed by few times of extraction with methylene chloride. The combined organic layer was dried over anhydrous magnesium sulfate, filtered and concentrated under reduced pressure. The residue was purified by column chromatography (silica gel, hexane:ethyl acetate=1:3), thereby completing the preparation of a target compound (159 mg, 50% yield).

¹H-NMR (300 MHz, CDCl₃), ppm (δ):7.36~7.22(m, 5H), 4.56(s, 2H), 4.11(d, 2H, J=6.9 Hz), 3.41~3.23(m, 5H), 2.12~1.56(m, 7H), 1.39~1.19(m, 4H), 0.93~0.75(m, 2H)

EXAMPLE 35

Synthesis of pyrrolidine-1-carboxylic acid 4-(pyridin-2-ylmethoxy)-cyclohexylmethyl ester

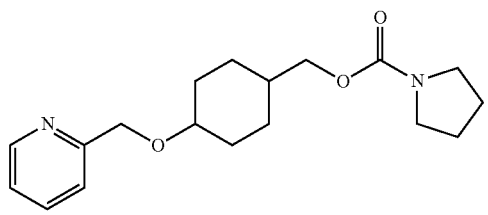 [SMILES: O=C(OCC1CCC(OCc2ccccn2)CC1)N1CCCC1]

A target compound (134 mg, 42% yield) was prepared in the same manner as in Example 34, except that 2-chloromethyl-pyridine was used as a starting material.

¹H-NMR (300 MHz, CDCl₃), ppm (δ):8.53(s, 1H, J=4.2 Hz), 7.72~7.65(m, 1H), 7.47(d, 1H, J=7.8 Hz), 7.21~7.13(m, 1H), 4.69(s, 2H), 3.89(d, 2H, J=6.3 Hz), 3.41~3.29(m, 5H), 2.19~2.10(m, 2H), 2.06~1.79(m, 6H), 1.66~1.59(m, 1H), 1.42~1.23(m, 2H), 1.17~0.98(m, 2H)

EXAMPLE 36

Synthesis of pyrrolidine-1-carboxylic acid 4-(1-oxy-pyridin-2-ylmethoxy)-cyclohexylmethyl ester

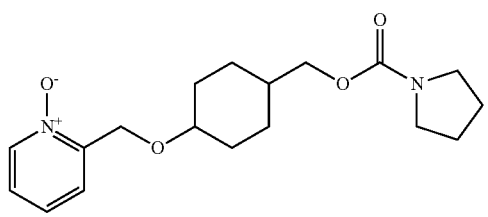 [SMILES: O=C(OCC1CCC(OCc2cccc[n+]2[O-])CC1)N1CCCC1]

A target compound (114 mg, 34% yield) was prepared in the same manner as in Example 34, except that 2-chloromethyl-pyridine 1-oxide was used as a starting material.

$^1$H-NMR (300 MHz, CDCl$_3$), ppm (δ):8.23(s, 1H, J=5.7 Hz), 7.59(s, 1H, J=7.8 Hz), 7.39~7.18(m, 2H), 4.82(s, 2H), 3.92(d, 2H, J=3.9 Hz), 3.48~3.30(m, 5H), 2.24~2.15(m, 2H), 2.05~1.80(m, 6H), 1.75~1.60(m, 1H), 1.45~1.23(m, 2H), 1.18~0.99(m, 2H)

EXAMPLE 37

Synthesis of pyrrolidine-1-carboxylic acid 4-benzylaminocyclohexylmethyl ester HCl salt

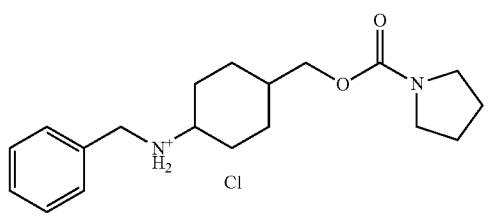

To a solution of pyrrolidine-1-carboxylic acid 4-hydroxy-cyclohexylmethyl ester (2 mmol) in methylene chloride (10 mL) were added TEMPO (0.2 mmol), tetrabutylammonium bromide (0.8 mmol), and oxone (4.4 mmol) and the resulting mixture was stirred for 14 hours. The reaction mixture was diluted with water, followed by few times of extraction with methylene chloride. The combined organic layer was dried over anhydrous magnesium sulfate, filtered and concentrated under reduced pressure. The residue was purified by column chromatography (silica gel, hexane:ethyl acetate=1:2) to provide pyrrolidine-1-carboxylic acid 4-oxo-cyclohexylmethyl ester. To a solution of pyrrolidine-1-carboxylic acid 4-oxo-cyclohexylmethyl ester in 1,2-dichloroethane (10 mL) were added benzyl amine (2 mmol) and sodium triacetoxyborohydride (2 mmol) and the resulting mixture was stirred for 14 hours. The reaction mixture was diluted with water, followed by few times of extraction with methylene chloride. The combined organic layer was dried over anhydrous magnesium sulfate, filtered and concentrated under reduced pressure. The residue was purified by column chromatography (silica gel, ethyl acetate), thereby completing the preparation of a target compound (399 mg, 63% yield). To a solution of the obtained compound in methylene chloride was added a saturated HCl solution in ether to provide a hydrochloride salt.

$^1$H-NMR (500 MHz, CDCl$_3$), ppm (δ):7.35-7.25(m, 5H), 4.0(d, 1H, J=6.3 Hz), 3.91-3.90(d, 1H, J=6.3 Hz), 3.85(s, 1H), 3.79(s, 1H), 3.40-3.35(m, 4H), 2.50(m, 1H), 2.04(m, 1H), 1.86-1.82(m, 6H), 1.55-1.51(m, 3H), 1.21-1.16(m, 1H), 1.08-1.03(m, 1H)

Examples 38 and 39 were each performed in the same manner as Example 37, except that the used starting material was different from the starting material used in Example 37.

EXAMPLE 38

Synthesis of pyrrolidine-1-carboxylic acid 4-(4-methoxy-benzylamino)-cyclohexylmethyl ester HCl salt

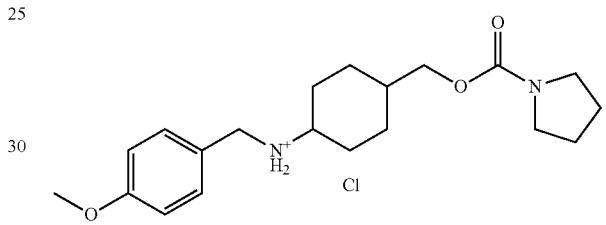

A target compound (460 mg, 60% yield) was prepared in the same manner as in Example 37, except that 4-methoxy-benzylamine was used as a starting material.

$^1$H-NMR (500 MHz, CDCl$_3$), ppm (δ):7.30-7.27(m, 2H), 6.88-6.86(m, 2H), 4.0-3.84(m, 2H), 3.80(s, 3H), 3.77-3.35 (m, 1H), 3.39-3.35(m, 4H), 1.87-1.82(m, 4H), 1.54-1.52(m, 4H), 1.35-1.32(m, 1H), 1.10-1.01(m, 1H)

EXAMPLE 39

Synthesis of pyrrolidine-1-carboxylic acid 4-[2-(4-methoxy-phenyl)-ethylamino]-cyclohexylmethyl ester HCl salt

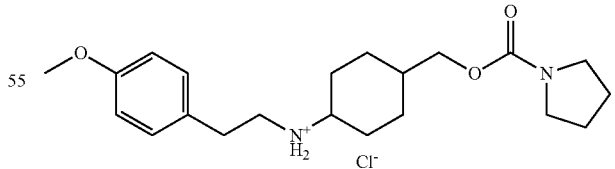

A target compound (516 mg, 65% yield) was prepared in the same manner as in Example 37, except that 2-(4-methoxy-phenyl)-ethylamine was used as a starting material.

$^1$H-NMR (500 MHz, CDCl$_3$), ppm (δ):7.15-7.13(m, 2H), 6.85-6.83(m, 2H), 3.97-3.83(m, 2H), 3.80(s, 3H), 3.40-3.32 (m, 4H), 2.86-2.77(m, 4H), 1.86-1.81(m, 6H), 1.61-1.46(m, 6H)

EXAMPLE 40

Synthesis of pyrrolidine-1-carboxylic acid 4-(pyridin-2-ylmethoxycarbonylamino)-cyclohexylmethyl ester

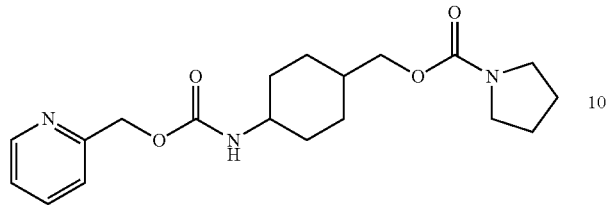

To a solution of pyrrolidine-1-carboxylic acid 4-oxo-cyclohexylmethyl ester (2 mmol) in ethanol (10 mL) was added hydroxylamine (10 mmol) and the mixture was refluxed for 5 hours. The reaction mixture was concentrated under reduced pressure, and the residue was dissolved in ethyl acetate and washed with water. The organic layer was dried over anhydrous magnesium sulfate, filtered and concentrated under reduced pressure to provide pyrrolidine-1-carboxylic acid 4-hydroxyimino-cyclohexylmethyl ester. Pyrrolidine-1-carboxylic acid 4-hydroxyimino-cyclohexylmethyl ester was dissolved in a 2N ammonia methanol solution (10 mL) and then Raney nickel was added. After 12 hours stirring under hydrogen atmosphere, the reaction mixture was filtered and concentrated under reduced pressure to provide pyrrolidine-1-carboxylic acid 4-amino-cyclohexylmethyl ester. To a solution of pyridine-2-yl-methanol (2 mmol) in THF (10 mL) was added CDI (2 mmol). After 2 h stirring at room temperature, pyrrolidine-1-carboxylic acid 4-amino-cyclohexylmethyl ester was added and the resulting mixture was stirred for additional 2 hours at 60° C. The reaction mixture was diluted with water, followed by few times of extraction with methylene chloride. The combined organic layer was dried over anhydrous magnesium sulfate, filtered and concentrated under reduced pressure. The residue was purified by column chromatography (silica gel, ethyl acetate), thereby completing the preparation of a target compound (310 mg, 43% yield).

$^1$H-NMR (300 MHz, CDCl$_3$), ppm (δ): 8.43~8.39(m, 1H), 7.78~7.65(m, 1H), 7.39~7.30(m, 1H), 7.26~7.20(m, 1H), 5.21(s, 2H), 4.82(d, 2H, J=8.3 Hz), 3.98~3.80(m, 2H), 3.53~3.26(m, 5H), 2.13~1.56(m, 9H), 1.37~1.03(m, 4H)

Examples 41 to 53 were each performed in the same manner as Example 40, except that the used starting material was different from the starting material used in Example 40.

EXAMPLE 41

Synthesis of pyrrolidine-1-carboxylic acid 4-(pyridin-3-ylmethoxycarbonylamino)-cyclohexylmethyl ester

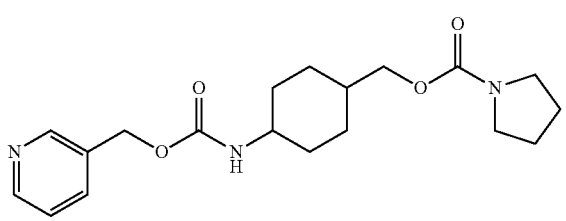 [SMILES: O=C(NC1CCC(COC(=O)N2CCCC2)CC1)OCc1cccnc1]

A target compound (289 mg, 40% yield) was prepared in the same manner as in Example 40, except that pyridin-3-yl-methanol was used as a starting material.

$^1$H-NMR (300 MHz, CDCl$_3$), ppm (δ): 8.65(s, 1H), 8.61~8.52(m, 1H), 7.73~7.69(m, 1H), 7.33~7.26(m, 1H), 5.11(s, 2H), 4.76(d, 2H, J=8.3 Hz), 3.99~3.75(m, 2H), 3.51~3.23(m, 5H), 2.12~1.52(m, 9H), 1.42~1.05(m, 4H)

EXAMPLE 42

Synthesis of pyrrolidine-1-carboxylic acid 4-(pyridin-4-ylmethoxycarbonylamino)-cyclohexylmethyl ester

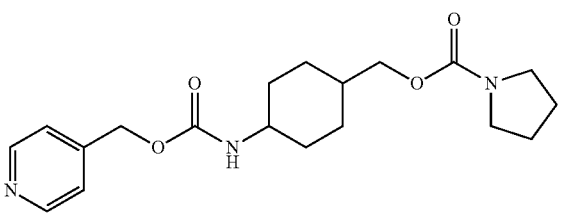

A target compound (282 mg, 39% yield) was prepared in the same manner as in Example 40, except that pyridin-4-yl-methanol was used as a starting material.

$^1$H-NMR (300 MHz, CDCl$_3$), ppm (δ): 8.61~8.56(m, 2H), 7.27~7.22(m, 2H), 5.11(s, 2H), 4.76(d, 2H, J=9.0 Hz), 3.98~3.89(m, 2H), 3.53~3.26(m, 5H), 2.13~1.99(m, 1H), 1.94~1.56(m, 8H), 1.22~1.05(m, 4H)

EXAMPLE 43

Synthesis of pyrrolidine-1-carboxylic acid 4-(2-chloro-pyridin-4-ylmethoxycarbonylamino)-cyclohexylmethyl ester

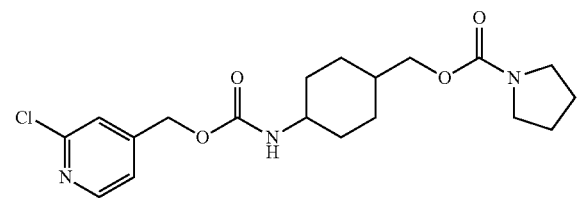 [SMILES: O=C(NC1CCC(COC(=O)N2CCCC2)CC1)OCc1ccnc(Cl)c1]

A target compound (348 mg, 44% yield) was prepared in the same manner as in Example 40, except that (2-chloro-pyridin-4-yl)-methanol was used as a starting material.

$^1$H-NMR (300 MHz, CDCl$_3$), ppm (δ): 8.36(d, 1H, J=4.8 Hz), 7.30(s, 1H), 7.19~7.13(m, 2H), 5.09(s, 2H), 5.01(d, 2H, J=8.7 Hz), 4.00~3.79(m, 2H), 3.49~3.30(m, 5H), 1.97~1.59 (m, 9H), 1.38~1.09(m, 4H)

EXAMPLE 44

Synthesis of pyrrolidine-1-carboxylic acid 4-(2-chloro-pyridin-3-ylmethoxycarbonylamino)-cyclohexylmethyl ester

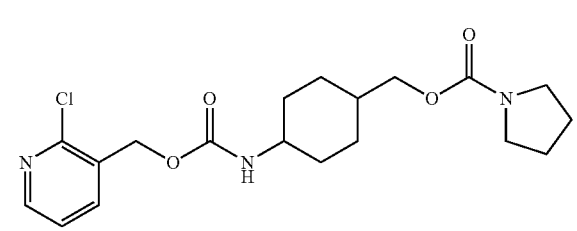

A target compound (356 mg, 45% yield) was prepared in the same manner as in Example 40, except that (2-chloro-pyridin-3-yl)-methanol was used as a starting material.

$^1$H-NMR (300 MHz, CDCl$_3$), ppm (δ): 8.38~8.32(m, 1H), 7.79~7.73(m, 1H), 7.30~7.22(m, 1H), 5.19(s, 2H), 5.01(d, 2H, J=8.4 Hz), 3.99~3.87(m, 2H), 3.52~3.26(m, 5H), 1.96~1.57(m, 9H), 1.38~1.09(m, 4H)

EXAMPLE 45

Synthesis of pyrrolidine-1-carboxylic acid 4-(2,6-dichloro-pyridin-4-ylmethoxycarbonylamino)-cyclohexylmethyl ester

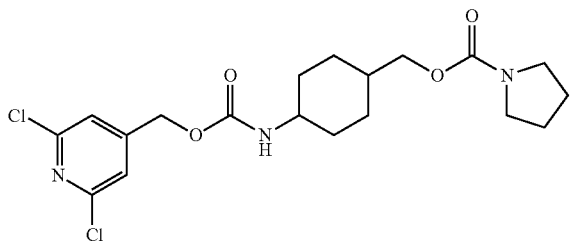 [SMILES: O=C(NC1CCC(COC(=O)N2CCCC2)CC1)OCc1cc(Cl)nc(Cl)c1]

A target compound (336 mg, 39% yield) was prepared in the same manner as in Example 40, except that (2,6-dichloro-pyridin-4-yl)-methanol was used as a starting material.

$^1$H-NMR (300 MHz, CDCl$_3$), ppm (δ): 7.22(s, 2H), 5.09(s, 2H), 4.82(d, 1H, J=12.5 Hz), 3.92(d, 2H, J=8.1 Hz), 3.53~3.29(m, 5H), 2.17~2.02(m, 2H), 1.96~1.56(m, 7H), 1.37~1.06(m, 4H)

EXAMPLE 46

Synthesis of pyrrolidine-1-carboxylic acid 4-(6-chloro-pyridin-2-ylmethoxycarbonylamino)-cyclohexylmethyl ester

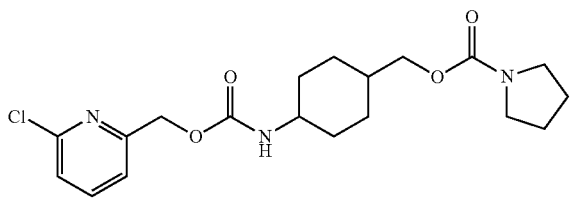 [SMILES: O=C(NC1CCC(COC(=O)N2CCCC2)CC1)OCc1cccc(Cl)n1]

A target compound (301 mg, 38% yield) was prepared in the same manner as in Example 40, except that (6-chloro-pyridin-2-yl)-methanol was used as a starting material.

$^1$H-NMR (300 MHz, CDCl$_3$), ppm (δ): 7.71~7.61(m, 1H), 7.31~7.22(m, 2H), 5.16(s, 2H), 4.89(d, 1H, J=8.4 Hz), 3.99~3.82(m, 2H), 3.49~3.29(m, 5H), 2.15~1.57(m, 9H), 1.37~1.05(m, 4H)

EXAMPLE 47

Synthesis of pyrrolidine-1-carboxylic acid 4-(6-chloro-pyridin-3-ylmethoxycarbonylamino)-cyclohexylmethyl ester

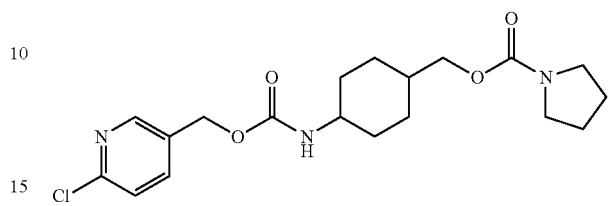

A target compound (348 mg, 44% yield) was prepared in the same manner as in Example 40, except that (6-chloro-pyridin-3-yl)-methanol was used as a starting material.

$^1$H-NMR (300 MHz, CDCl$_3$), ppm (δ): 8.39(s, 1H), 7.70~7.65(m, 1H), 7.35~7.29(m, 1H), 5.07(s, 2H), 4.78(d, 2H, J=8.1 Hz), 3.97~3.87(m, 2H), 3.49~3.27(m, 5H), 2.14~1.52(m, 9H), 1.37~1.03(m, 4H)

EXAMPLE 48

Synthesis of pyrrolidine-1-carboxylic acid 4-(2-methyl-pyridin-3-ylmethoxycarbonylamino)-cyclohexylmethyl ester

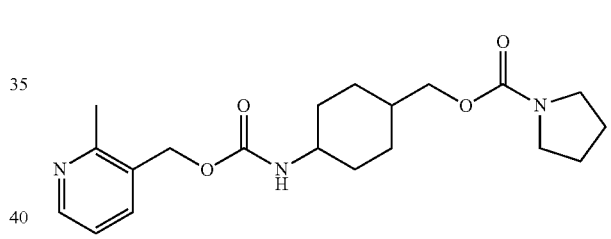

A target compound (345 mg, 46% yield) was prepared in the same manner as in Example 40, except that (2-methyl-pyridin-3-yl)-methanol was used as a starting material.

$^1$H-NMR (300 MHz, CDCl$_3$), ppm (δ): 8.45~8.43(m, 1H), 7.64~7.58(m, 1H), 7.20~7.08(m, 1H), 5.10(s, 2H), 4.94(d, 1H, J=8.1 Hz), 3.96~3.87(m, 2H), 3.53~3.26(m, 5H), 2.56(s, 3H), 2.25~1.53(m, 9H), 1.40~1.05(m, 4H)

EXAMPLE 49

Synthesis of pyrrolidine-1-carboxylic acid 4-(6-methyl-pyridin-2-ylmethoxycarbonylamino)-cyclohexylmethyl ester

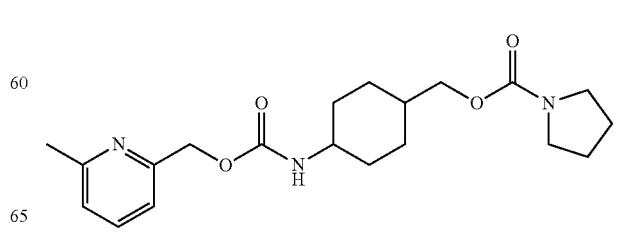

A target compound (353 mg, 47% yield) was prepared in the same manner as in Example 40, except that (6-methyl-pyridin-2-yl)-methanol was used as a starting material.

¹H-NMR (300 MHz, CDCl₃), ppm (δ): 7.62~7.54(m, 1H), 7.15(d, 1H, J=7.5 Hz), 7.08(d, 1H, J=7.5 Hz), 5.16(s, 2H), 4.82~4.73(m, 1H), 3.96~3.87(m, 2H), 3.52~3.24(m, 5H), 2.56(s, 3H), 2.17~1.53(m, 9H), 1.38~1.03(m, 4H)

EXAMPLE 50

Synthesis of pyrrolidine-1-carboxylic acid 4-(6-trifluoromethyl-pyridin-3-ylmethoxycarbonylamino)-cyclohexylmethyl ester

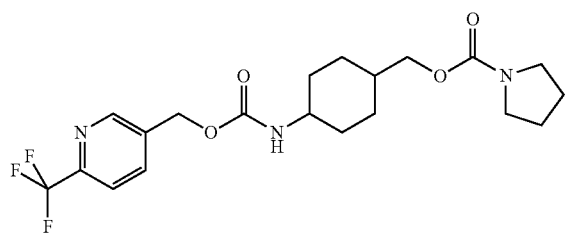 [SMILES: O=C(NC1CCC(COC(=O)N2CCCC2)CC1)OCc1ccc(C(F)(F)F)nc1]

A target compound (352 mg, 41% yield) was prepared in the same manner as in Example 40, except that (6-trifluoromethyl-pyridin-3-yl)-methanol was used as a starting material.

¹H-NMR (300 MHz, CDCl₃), ppm (δ): 8.72(s, 1H), 7.87(d, 1H, J=8.1 Hz), 7.68(d, 1H, J=8.1 Hz), 5.18(s, 2H), 4.70(d, 1H, J=6.8 Hz), 3.90(d, 2H, J=6.3 Hz), 3.52~3.25(m, 4H), 2.15~1.52(m, 10H), 1.44~1.05(m, 4H)

EXAMPLE 51

Synthesis of pyrrolidine-1-carboxylic acid 4-(1-oxy-pyridin-2-ylmethoxycarbonylamino)-cyclohexylmethyl ester

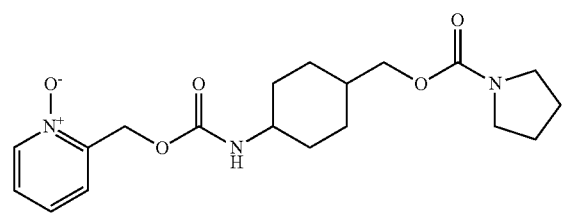 [SMILES: O=C(NC1CCC(COC(=O)N2CCCC2)CC1)OCc1cccc[n+]1[O-]]

A target compound (264 mg, 35% yield) was prepared in the same manner as in Example 40, except that (1-oxy-pyridin-2-yl)-methanol was used as a starting material.

¹H-NMR (500 MHz, CDCl₃), ppm (δ): 8.20-8.18(d, 1H, J=6.3 Hz), 7.34-7.17(m, 3H), 5.38-5.36(d, 1H, J=6.3 Hz), 5.28(s, 2H), 3.91-3.76(m, 2H), 3.41-3.38(m, 1H), 3.33-3.26(m, 4H), 2.56(s, 1H), 2.0-1.98(d, 1H, J=6.3 Hz), 1.83-1.75(m, 6H), 1.67-1.65(m, 1H), 1.59-1.55(m, 2H), 1.30-1.17(m, 5H)

EXAMPLE 52

Synthesis of pyrrolidine-1-carboxylic acid 4-(1-oxy-pyridin-3-ylmethoxycarbonylamino)-cyclohexylmethyl ester

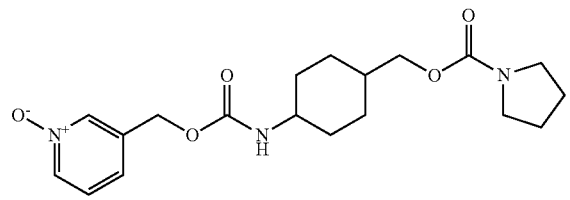 [SMILES: O=C(NC1CCC(COC(=O)N2CCCC2)CC1)OCc1ccc[n+]([O-])c1]

A target compound (249 mg, 33% yield) was prepared in the same manner as in Example 40, except that (1-oxy-pyridin-3-yl)-methanol was used as a starting material.

¹H-NMR (500 MHz, CDCl₃), ppm (δ): 8.23-8.22(d, 1H, J=6.3 Hz), 8.12(s, 1H), 7.27-7.23(m, 2H), 5.47-5.27(m, 1H), 2.01(s, 2H), 3.93-3.91(d, 1H, J=6.3 Hz), 3.39-3.29(m, 5H), 2.04(s, 1H), 2.01-1.99(m, 1H), 1.85-1.81(m, 6H), 1.75-1.57(m, 4H), 1.31-1.18(m, 5H)

EXAMPLE 53

Synthesis of pyrrolidine-1-carboxylic acid 4-(1-oxy-pyridin-4-ylmethoxycarbonylamino)-cyclohexylmethyl ester

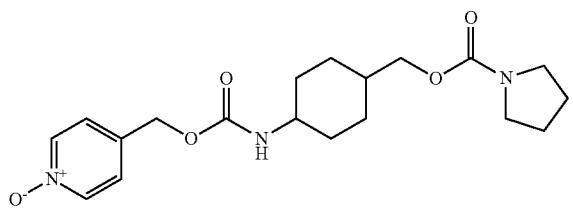 [SMILES: O=C(NC1CCC(COC(=O)N2CCCC2)CC1)OCc1cc[n+]([O-])cc1]

A target compound (257 mg, 34% yield) was prepared in the same manner as in Example 40, except that (1-oxy-pyridin-4-yl)-methanol was used as a starting material.

¹H-NMR (500 MHz, CDCl₃), ppm (δ): 8.19-8.17(m, 2H), 7.26-7.23(m, 2H), 5.00(s, 2H), 3.96-3.95(d, 1H, J=6.3 Hz), 3.91-3.89(d, 1H, J=6.3 Hz), 3.36-3.31(m, 4H), 2.05-2.03(m, 2H), 1.93(s, 2H), 1.93-1.84(m, 6H), 1.69-1.61(m, 3H), 1.33-1.13(m, 8H)

EXAMPLE 54

Synthesis of pyridin-4-ylmethyl-carbamic acid 4-{[(pyrrolidine-1-carbonyl)-amino]-methyl}-cyclohexyl ester

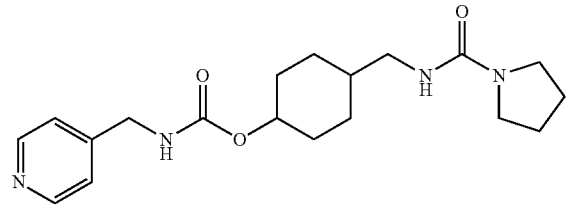

To a solution of 4-hydroxymethylcyclohexanol (2 mmol) in THF (10 mL) were added Ms-Cl (2.2 mmol) and triethylamine (3 mmol) at 0° C. and the resulting mixture was stirred for 2 hours. The reaction mixture was concentrated under reduced pressure, and the residue was dissolved in ethyl acetate and washed with water. The organic layer was dried over anhydrous magnesium sulfate, filtered and concentrated under reduced pressure. The residue was dissolved in 10 mL of DMF, and then $NaN_3$ (6 mmol) was added. After overnight stirring at 60° C., the reaction mixture was diluted with ethyl acetate and washed with water. The organic layer was dried over anhydrous magnesium sulfate, filtered and concentrated under reduced pressure. Then, the obtained compound was dissolved in methanol, and 10% Pd—C (0.2 mmol) was added. After overnight stirring under hydrogen atmosphere, the reaction mixture was filtered, washed with methanol and concentrated under reduced pressure to provide 4-aminomethyl-cyclohexanol. To a solution of 4-aminomethyl-cyclohexanel in dichloromethane (10 mL) were added 1-pyrrolidinecarbonyl chloride (2 mmol) and triethylamine (3 mmol). After overnight stirring at room temperature, the reaction mixture was diluted with water, followed by few times of extraction with methylene chloride. The combined organic layer was dried over anhydrous magnesium sulfate, filtered and concentrated under reduced pressure. The residue was purified by column chromatography (silica gel, hexane:ethyl acetate=1:1) to provide a pyrrolidine-1-carboxylic acid (4-hydroxy-cyclohexylmethyl)-amide. The pyrrolidine-1-carboxylic acid (4-hydroxy-cyclohexylmethyl)-amide compound was dissolved in acetonitrile (10 mL), and then CDI (2.2 mmol) was added. After 1 hours stirring at 80° C., methyl iodide (10 mmol) was added and stirred for additional 1 hour at 80° C. The reaction mixture was concentrated under reduced pressure, and the residue was dissolved in acetonitrile (10 mL) and C-pyridine-2-yl-methylamine (3 mmol) was added. After 4 hours stirring at 80° C., the reaction mixture was diluted with water, followed by few times of extraction with methylene chloride. The combined organic layer was dried over anhydrous magnesium sulfate, filtered and concentrated under reduced pressure. The residue was purified by column chromatography (silica gel, hexane:ethyl acetate=1:3), thereby completing the preparation of a target compound (180 mg, 25% yield).

$^1$H-NMR (300 MHz, $CDCl_3$), ppm (δ): 8.50~8.46(m, 2H), 7.13(d, 2H, J=6.0 Hz), 5.10(bs, 1H), 4.58~4.43(m, 1H), 4.35~4.25(m, 3H), 3.28~3.21(m, 4H), 3.03~2.99(m, 2H), 2.35~1.66(m, 7H), 1.51~1.13(m, 4H), 1.08~0.92(m, 2H)

Example 55 was performed in the same manner as Example 54, except that the used starting material was different from the starting material used in Example 54.

EXAMPLE 55

Synthesis of pyridin-4-ylmethyl-carbamic acid 4-[(cyclopentanecarbonyl-amino)-methyl]-cyclohexyl ester

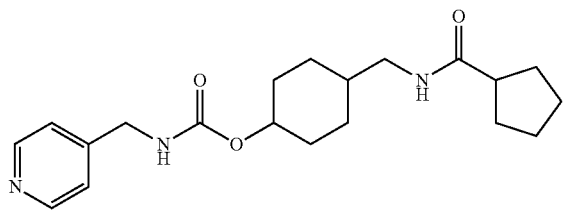 [SMILES: O=C(NCc1ccncc1)OC1CCC(CNC(=O)C2CCCC2)CC1]

A target compound (144 mg, 20% yield) was prepared in the same manner as in Example 54, except that cyclopentanecarbonyl chloride was used as a starting material.

$^1$H-NMR (300 MHz, $CDCl_3$), ppm (δ): 8.47~8.41(m, 2H), 7.20~7.11(m, 2H), 5.79~5.61(m, 1H), 5.46~5.37(m, 1H), 4.57~4.42(m, 1H), 4.30(d, 2H, J=6.0 Hz), 3.09~2.99(m, 2H), 2.52~2.38(m, 1H), 2.26~2.11(m, 1H), 2.03~1.93(m, 1H), 1.83~1.60(m, 7H), 1.59~1.38(m, 4H), 1.33~1.14(m, 2H), 1.17~0.89(m, 2H)

EXAMPLE 56

LPS-Induced NO Production Inhibition Test

Mouse monocytes (RAW) and mouse microglia (BV2) cells were cultured on a 96-well transparent plate (Nunc) in such a way that each of the wells contained 60,000 and 35,000 cells respectively. After 18 hours, when stabilized, the cells were treated with lipopolysaccharide (Sigma, USA, Cat No. L2630) in a morbid state derived from 20 ng/ml of *Escherichia coli* O111:B4 and 4 different concentrations (50 uM, 12.5 uM, 3.1 uM, and 0.8 uM) of the compounds synthesized according to Examples 1 to 55. Then, the cells were cultured for 24 hours, and a concentration of increased NO was measured. The NO concentration was determined by measuring absorption at a wavelength of 540 nm after a Griess reagent including 0.1% N-(1-naphthyl)ethylenediamine dihydrochloride, 1% sulfanilamide, and 2.5% phosphoric acid were added thereto. It was confirmed by measuring the NO concentration ($IC_{50}$, uM) that the compounds inhibit production of NO, and results thereof are shown in Table 1 below.

TABLE 1

| Compound | Monocyte (RAW) | Microglia (BV2) |
|---|---|---|
| Example 1 | 27.9 | 19.9 |
| Example 2 | >50 | 40.1 |
| Example 3 | 22.3 | 30.3 |
| Example 4 | 30.3 | 32.9 |
| Example 5 | >50 | 48.7 |
| Example 6 | 41.2 | >50 |
| Example 7 | >50 | >50 |
| Example 8 | >50 | 5.8 |
| Example 9 | >50 | >50 |
| Example 10 | 46.1 | 5.3 |
| Example 11 | 10.2 | >50 |
| Example 12 | >50 | >50 |
| Example 13 | 27.9 | >50 |
| Example 14 | 21.7 | 22.3 |
| Example 15 | 19.9 | 19.4 |
| Example 16 | 27.9 | 10.8 |
| Example 17 | 29.5 | 12.5 |
| Example 18 | 5.7 | 18.3 |
| Example 19 | 11.1 | 13.8 |
| Example 20 | 50 | 37.9 |
| Example 21 | 15.9 | 44.8 |
| Example 22 | 35.8 | 21.7 |
| Example 23 | 28.6 | >50 |
| Example 24 | >50 | >50 |
| Example 25 | 24.9 | 15.5 |
| Example 26 | 46.1 | 36.8 |
| Example 27 | 50.0 | >50 |
| Example 28 | >50 | 44.8 |
| Example 29 | 46.1 | >50 |
| Example 30 | >50 | >50 |
| Example 31 | >50 | 21.1 |
| Example 32 | 21.1 | 34.8 |
| Example 33 | >50 | >50 |
| Example 34 | 24.9 | 27.1 |
| Example 35 | >50 | 50.0 |
| Example 36 | >50 | >50 |
| Example 37 | 46.1 | >50 |
| Example 38 | 35.8 | >50 |

TABLE 1-continued

| Compound | Monocyte (RAW) | Microglia (BV2) |
| --- | --- | --- |
| Example 39 | >50 | >50 |
| Example 40 | >50 | >50 |
| Example 41 | 50 | >50 |
| Example 42 | 50 | >50 |
| Example 43 | 10.5 | 12.0 |
| Example 44 | 21.7 | 16.8 |
| Example 45 | 9.9 | 7.5 |
| Example 46 | 32.0 | 26.3 |
| Example 47 | 13.1 | 21.1 |
| Example 48 | 13.5 | 10.2 |
| Example 49 | 12.0 | 10.2 |
| Example 50 | 5.7 | 14.2 |
| Example 51 | 50 | >50 |
| Example 52 | 22.3 | >50 |
| Example 53 | 33.9 | >50 |
| Example 54 | 48.7 | >50 |
| Example 55 | 25.6 | >50 |

EXAMPLE 57

Pain Relief Test Using Animal Model

1) Animal Model

Male rats (Sprague-Dawley, 150-200 g, 6-week old, Orient Bio Co., Ltd) were purchased and acclimated in an animal chamber for one week. The animal chamber was alternately turned on and off at a time interval of 12 hours, at a temperature of 22 to 25° C., and in a relative humidity of 40-60%, and water and feed was supplied ad libitum to the rats.

2) Behavior Test: Mechanical Allodynia

The rats were placed in a round acryl container (5.5 15, 6.5 18 cm, which varied according to the size of body) and only the tails thereof were taken out of the container and placed on a plate. To confirm a pain behavior corresponding to a mechanical stimulus, an up-down method (*J. Neurosci. Methods* 53:55-63) was performed using a von Frey filament so as to measure "50% tail withdrawal threshold.

3) Induction of Neuropathic Pain

To screen out the rats that have pain in a normal state, "50% tail withdrawal threshold" of the normal rats that did not undergo a surgery was measured, and a caudal nerve damage surgery was performed on only the rats that exhibited the withdrawal threshold of 15 g or more. During all the steps before surgery, anesthesia was maintained with a mixed gas including 2-3% enflurane and 95% oxygen. To induce neuropathic pain, superior and inferior caudal trunks of the tails of the rats were exposed, and as illustrated in FIG. 1, a portion between the first and second sacral nerves was cut to a size of 1 to 2 mm (*Neurosci. Lett.* 177:50-52).

4) Drug Treatment

To select only the rats that certainly had the induced pain, rats that had a 50% tail withdrawal threshold of 0.25 g or less at a time of 2 weeks after the surgery were treated with medications. The compounds were each prepared as a solution form by using 5% DMSO, 5% Cremophore, and 90% distilled water on a volumetric basis. Each of the solutions was intraperitoneally administered in a volume of 3 ml per kg of a rat. The concentration of the compounds was controlled according to a compound and the concentration of reference was 30 mg/kg. After the administration, "50% tail withdrawal threshold" was measured at time intervals of 0, 1, 4, and 24 hours.

5) Statistics

Anti-allodynic effects of the compounds were described as mean±SEM, and were compared each other by referring to "% MPE (the percentage of maximum possible effect)," and analyzed using one-way ANOVA and Bonferroni's t-test. When the data had a difference of $p<0.05$, it was evaluated there is significance. [% MPE=(the threshold with respect to time after the drug treatment−the threshold at 0 hr)/(15−the threshold at 0 hr)×100]

Pain relief test results obtained by applying the compounds to the animals are shown in Table 2.

Table 2

TABLE 2

| Example No. | Pain test results |
| --- | --- |
| Example 8 | 11% at 1 hour |
| Example 9 | 64% at 0.5 hours |
| Example 13 | 35.3% at 2 hours |
| Example 15 | 29.2% at 1 hour |
| Example 16 | 16.4% at 4 hours |
| Example 17 | 5.8% at 1 hour |
| Example 18 | 22.5% at 1 hour |
| Example 20 | 22% at 4 hours |
| Example 21 | 35.2% at 1 hour |
| Example 23 | 18.7% at 4 hours |
| Example 40 | 11% at 4 hours |
| Example 42 | 57% at 4 hours |
| Example 54 | 10.5% at 1 hour |

The invention claimed is:

1. A compound selected from the group consisting of a methylcyclohexane derivative represented by Formula I below and a pharmaceutically acceptable salt, isomer, solvate, or hydrate thereof, or any combination thereof:

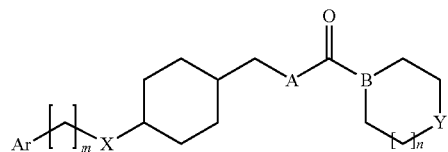

Formula I wherein:
Ar is selected from the group consisting of phenyl, pyridine, and pyridine-N-oxide, each of which is substituted with one or more identical or different substituents selected from the group consisting of a hydrogen atom, a linear or branched C1 to C6 alkyl, halogen, a linear or branched C1 to C6 alkoxy, and trifluoromethyl;
X is O, (C=O)O, $NR_1$(C=O)O, NH, (C=O)NH, or O(C=O)NH;
$R_1$ is H or CH3;
Y is $CH_2$, O, or N—$R_2$;
$R_2$ is H or $CH_3$;
A is O or NH;
B is CH or N; and
m is an integer between 0 and 2 and n is 0 or 1.

2. The compound of claim 1, wherein the compound has one of the following structures:

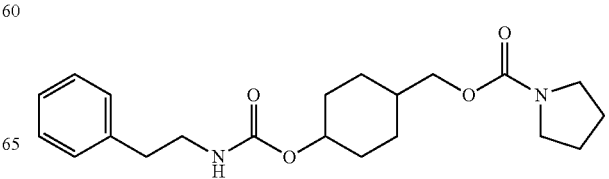

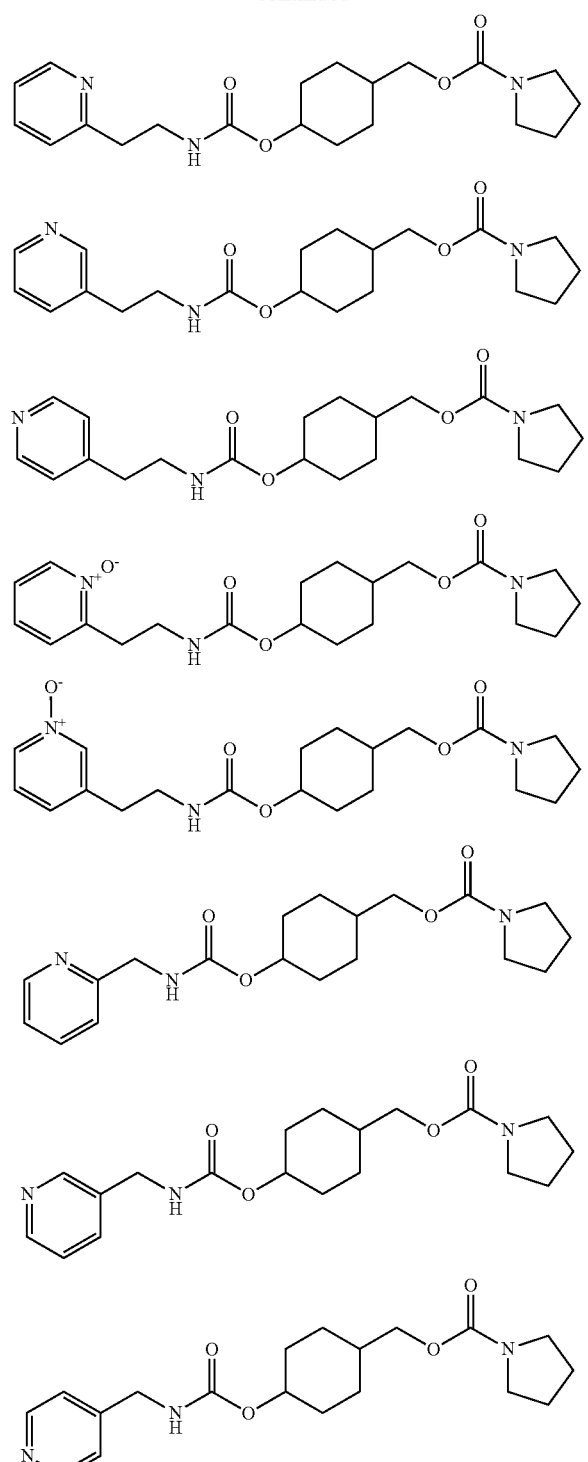
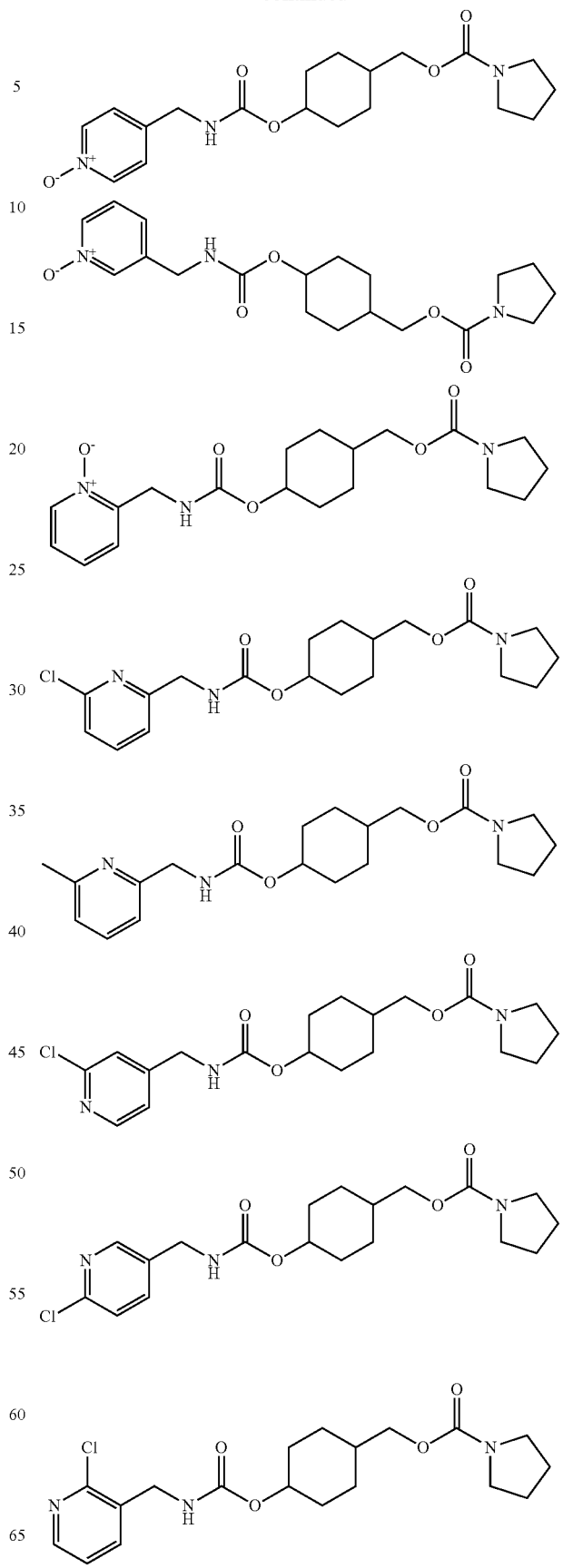

43
-continued
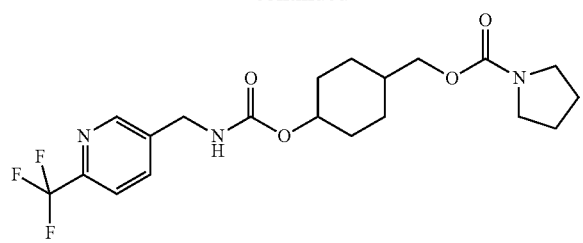
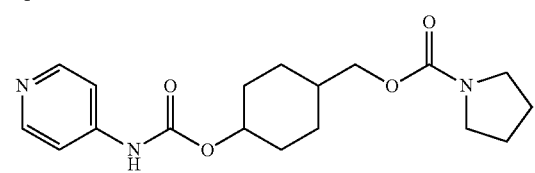
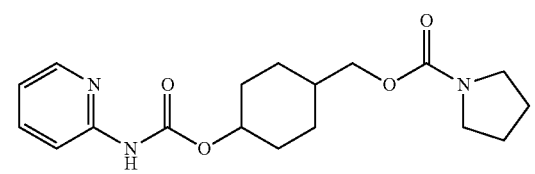
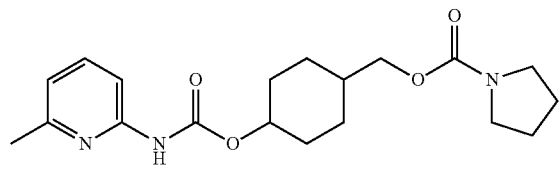
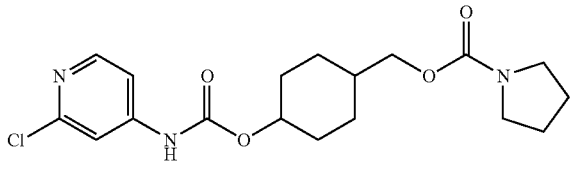
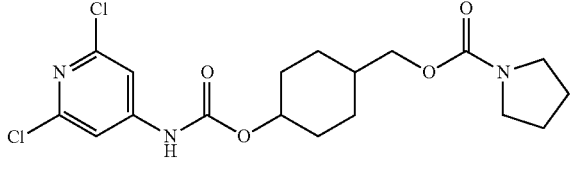
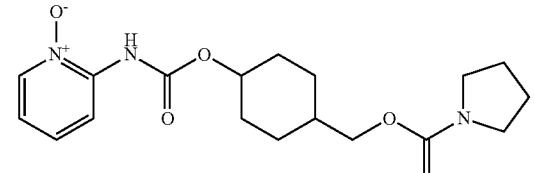
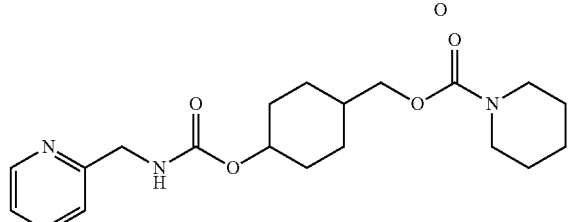
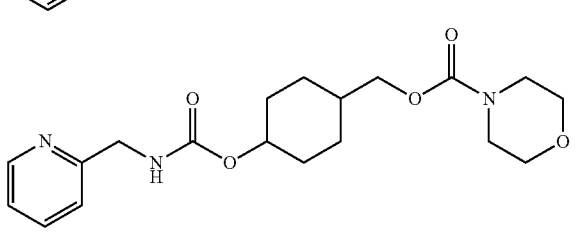
44
-continued
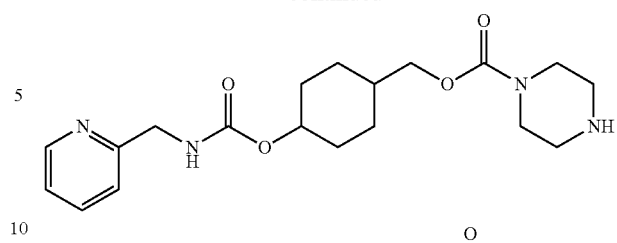
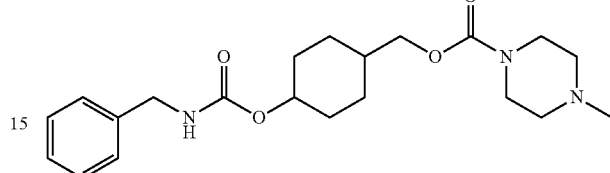
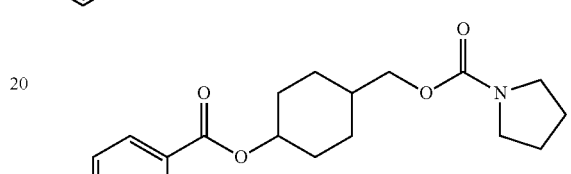
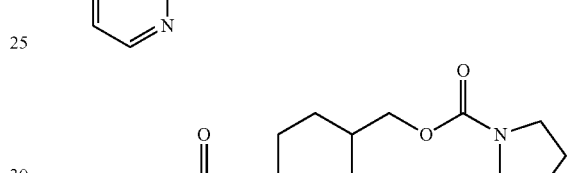
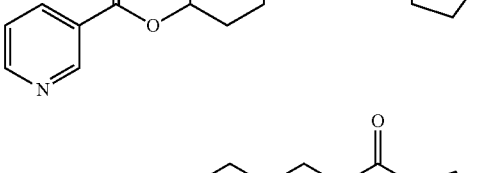
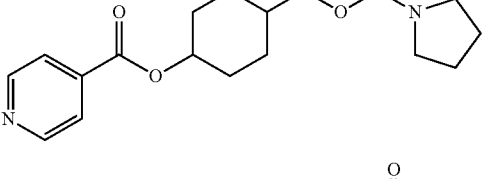
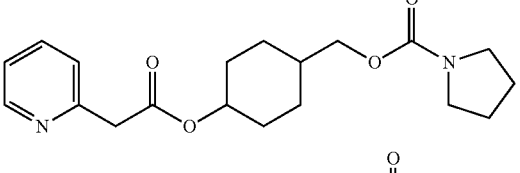
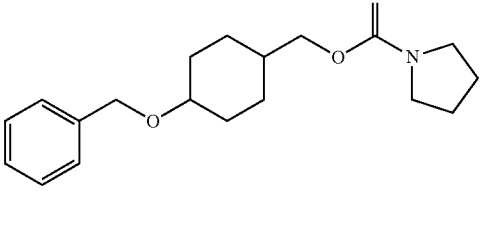
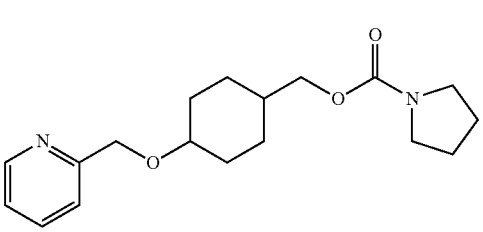

-continued
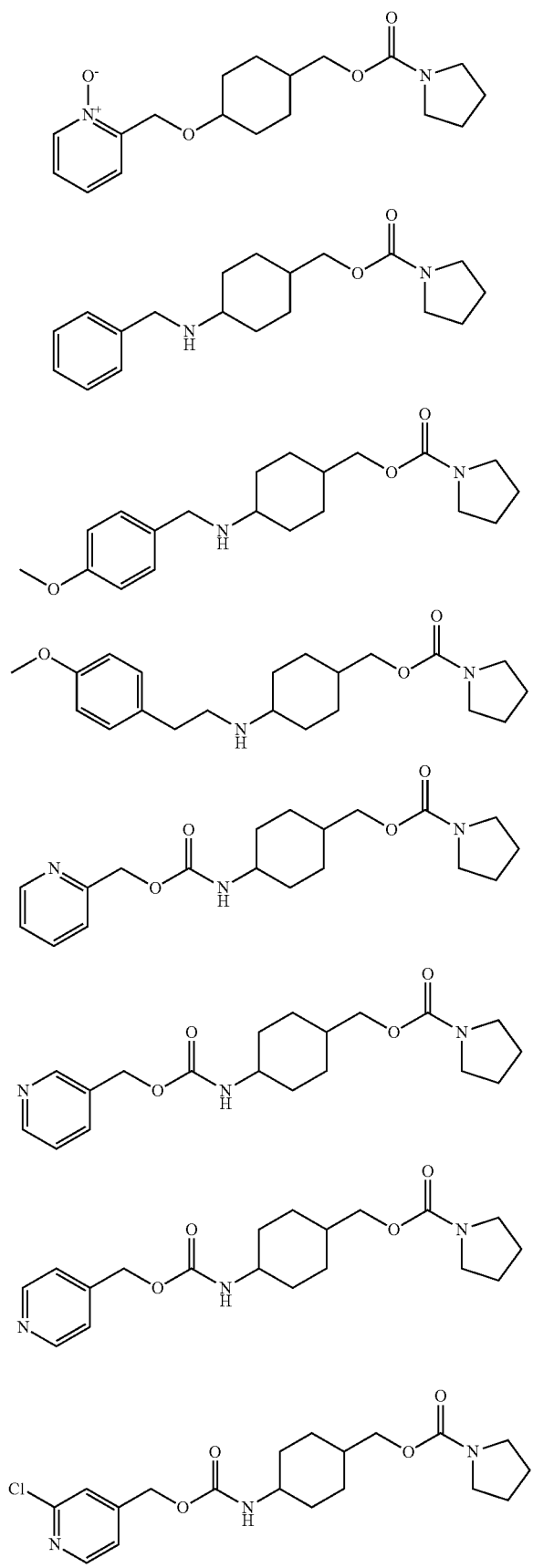
-continued
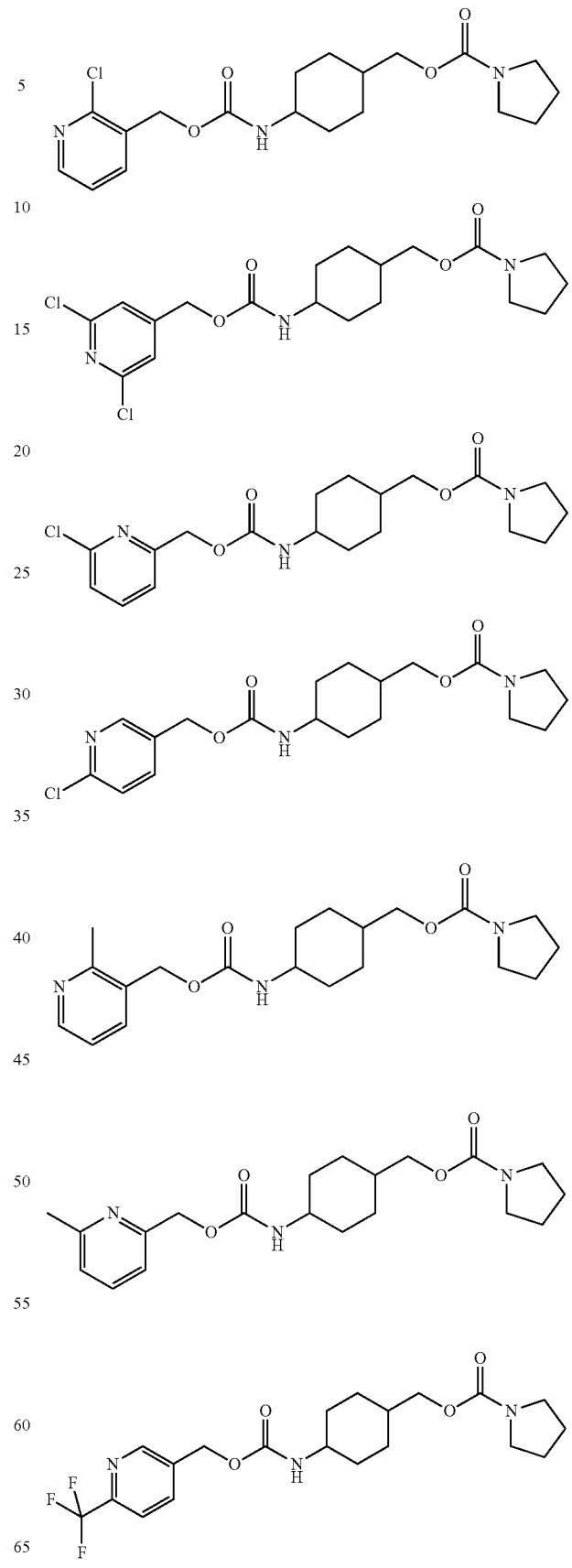

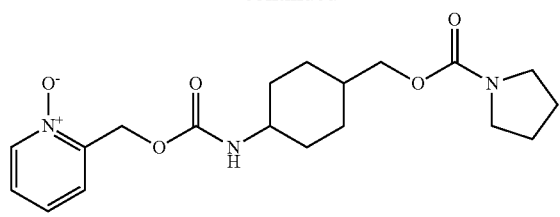
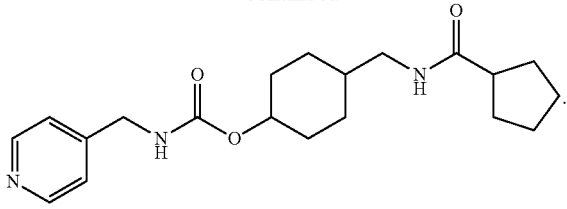

3. A pharmaceutical composition for the prevention or treatment of pain, the pharmaceutical composition comprising: a therapeutically effective amount of the methylcyclohexane derivative of claim 1; and a pharmaceutically acceptable carrier.

4. The pharmaceutical composition of claim 3, wherein the pain is acute pain or chronic pain.

5. The pharmaceutical composition of claim 3, wherein the pain is selected from the group consisting of cancer pain, labor pain, colic pain, neuropathic pain, postoperative pain, diabetic pain, post-herpetic pain, inflammatory disease pain, muscle pain, arthrodynia pain, a headache, and periodontal disease pain.

6. A method of treating pain, the method comprising contacting the pharmaceutical composition of claim 3 and a subject.

7. The method of claim 6, wherein the pain is acute pain or chronic pain.

8. The method claim 6, wherein the pain is selected from the group consisting of cancer pain, labor pain, colic pain, neuropathic pain, postoperative pain, diabetic pain, post-herpetic pain, inflammatory disease pain, muscle pain, arthrodynia pain, a headache, and periodontal disease pain.

* * * * *